US009476031B2

(12) United States Patent
Prieur et al.

(10) Patent No.: US 9,476,031 B2
(45) Date of Patent: Oct. 25, 2016

(54) METHOD FOR REJUVENATING CELLS

(75) Inventors: Alexandre Prieur, Montpellier (FR);
Ollivier Milhavet, Montpellier (FR);
Jean-Marc Lemaitre, Montpellier (FR); Laure Lapasset, Montpellier (FR)

(73) Assignees: Institut National de la Santé et de la Recherche Médicale (INSERM), Paris (FR); CENTRE NATIONAL DE LA RECHERCHE SCIENTIFIQUE (CNRS), Paris (FR); UNIVERSITE MONTPELLIER I, Montpellier (FR); UNIVERSITE MONTPELLIER II, Montpellier (FR)

( * ) Notice: Subject to any disclaimer, the term of this patent is extended or adjusted under 35 U.S.C. 154(b) by 47 days.

(21) Appl. No.: 14/009,662

(22) PCT Filed: Apr. 10, 2012

(86) PCT No.: PCT/EP2012/056409
§ 371 (c)(1),
(2), (4) Date: Oct. 31, 2013

(87) PCT Pub. No.: WO2012/136841
PCT Pub. Date: Oct. 11, 2012

(65) Prior Publication Data
US 2014/0056860 A1    Feb. 27, 2014

(30) Foreign Application Priority Data

Apr. 8, 2011    (EP) .................................... 11161771

(51) Int. Cl.
A01N 63/00    (2006.01)
A61K 48/00    (2006.01)
C12N 5/00    (2006.01)
C12N 5/02    (2006.01)
C12N 5/074    (2010.01)
A61K 35/12    (2015.01)

(52) U.S. Cl.
CPC ............ *C12N 5/0696* (2013.01); *A61K 35/12* (2013.01); *C12N 2501/602* (2013.01); *C12N 2501/603* (2013.01); *C12N 2501/604* (2013.01); *C12N 2501/605* (2013.01); *C12N 2501/606* (2013.01); *C12N 2501/608* (2013.01)

(58) Field of Classification Search
None
See application file for complete search history.

(56) References Cited

FOREIGN PATENT DOCUMENTS

EP    2 096 169 A1    9/2009
WO    2011/016588 A1    2/2011

OTHER PUBLICATIONS

Takahashi, 2006, Cell, 131:861-872.*
Meissner (Nature Biotechnology, 2007, 25:1177-1181.*
Stadtfeld , 2008, Cell, 2:230-240.*
Buganim, 2012,Cell, 150:1209-1222.*
Heng et al 2005a, Cell Tissue Res, 321:147-150.*
Heng, 2005b, Biomedicine and Pharmacotherapy, 59:132-134.*
Kim, 2009, Cell Stem Cell, 4:472-476.*
Zhou, Cell Stem Cell, 2009, 4:381-384.*
Warren, 2010, Cell Stem Cell, 7:618-630.*
Banito, Genes and Development, 2009,23:2134-2139.*
Thomson, Science, 282: 1145-1147, 1998.*
Reubinoff et al., 2000, Nature Biotechnology, vol. 18, pp. 399-404.*
Reijo et al., 2009, Differentiation, vol. 78, pp. 18-23.*
Remarks of Dr. Lyle Armstrong to the UK House of Parliaments' Select Committee on Science and Technology, Fifth Report of Session Jul. 2006, vol. II, pp. 76-77, Apr. 5, 2007.*
Dominiguez-Bendala et al., Handbook of Stem Cells, Chapter 70: Islet Cell Therapy and Pancreatic Stem Cells, pp. 835-853, 2013.*
Ressler, Aging Cell, 2006, 5:379-389.*
Lai et al., Proc Natl Acad Sci U S A. Mar. 6, 2012; 109(10):3772-7.*
Choi, Nature Biotechnology, 33:1173-1181, 2015.*
Robinton and Dailey, 2012, Nature, 481:295-305.*
Dimos et al., "Induced Pluripotent Stem Cells Generated from Patients with ALS Can Be Differentiated into Motor Neurons", Science, Aug. 29, 2008, pp. 1218-1221, vol. 231, No. 5893, American Association for the Advancement of Science, Washington, DC, US.
Yu et al., "Human Induced Pluripotent Stem Cells Free of Vector and Transgene Sequences", Science, May 8, 2009, vol. 324, No. 5928, American Association for the Advancement of Science, Washington, DC, US.
Hanna et al, "Direct cell reprogramming is a stochastic process amenable to acceleration", Nature, Dec. 3, 2009, pp. 595-601, vol. 462, No. 7273.
Badros et al., "Autologous stem cell transplantation in elderly multiple myeloma patients over the age of 70 years", British Journal of Haematology, Sep. 1, 2001, vol. 114, No. 3.
Bitran et al., "High-Dose Myeloablative Therapy and Autologous Peripheral Blood Progenitor Cell Transplantation for Elderly Patients (Greater than 65 Years of Age) with Relapsed Large Cell Lymphoma", Biology of Blood and Marrow Transplantation, Jun. 1, 2003, pp. 383-388, vol. 9, No. 6.
Lapasset et al., "Rejuvenating senescent and centenarian human cells by reprogramming through the pluripotent state", Genes and Development, Nov. 1, 2011, pp. 2248-2253, vol. 25, Cold Spring Harbor Laboratory Press, Plainview, NY, US.

* cited by examiner

*Primary Examiner* — Valarie Bertoglio
(74) *Attorney, Agent, or Firm* — Whitham, Curtis & Cook, P.C.

(57) ABSTRACT

The invention relates to a method for reprogramming cells from aged donors or senescent cells to pluripotent cells that have lost marks of senescence. In particular, the invention relates to an ex vivo method for preparing induced pluripotent stem cells (iPSCs) from a target cell population comprising cells from aged donors or senescent cells, said method comprising the steps of culturing said target cell population under appropriate conditions for reprogramming said cells into iPSCs, wherein said appropriate conditions comprises increasing expression in said target cells, of at least the following reprogramming factors: Oct4, Klf4, Sox2, c-Myc, Lin28 and, optionally Nanog.

12 Claims, No Drawings

SEQUENCE LISTING

```
<160> NUMBER OF SEQ ID NOS: 12

<210> SEQ ID NO 1
<211> LENGTH: 1411
<212> TYPE: DNA
<213> ORGANISM: homo sapiens

<400> SEQUENCE: 1
ccttcgcaag  ccctcatttc  accaggcccc  cggcttgggg  cgccttcctt  ccccatggcg      60
ggacacctgg  cttcggattt  cgccttctcg  cccccttccag  gtggtggagg  tgatgggcca    120 gggggccgg   agccggctg   ggttgatcct  cggacctggc  taagcttcca  aggccctcct    180
ggagggccag  gaatcgggcc  gggggttggg  ccaggctctg  aggtgtgggg  gattccccca    240
tgccccccgc  cgtatgagtt  ctgtgggggg  atggcgtact  gtgggcccca  ggttggagtg    300
gggctagtgc  cccaaggcgg  cttggagacc  tctcagcctg  agggcgaagc  aggagtcggg    360
gtggagagca  actccgatgg  ggcctccccg  gagccctgca  ccgtcacccc  tggtgccgtg    420
aagctggaga  aggagaagct  ggagcaaaac  ccggaggagt  cccaggacat  caaagctctg    480
```

```
cagaaagaac tcgagcaatt tgccaagctc ctgaagcaga agaggatcac cctgggatat      540
acacaggccg atgtggggct caccctgggg gttctatttg gaaggtatt cagccaaacg       600 accatctgcc gctttgaggc tctgcagctt agcttcaaga acatgtgtaa gctgcggccc     660
ttgctgcaga agtgggtgga ggaagctgac aacaatgaaa atcttcagga gatatgcaaa    720
gcagaaaccc tcgtgcaggc ccgaaagaga aagcgaacca gtatcgagaa ccgagtgaga    780
ggcaacctgg agaatttgtt cctgcagtgc ccgaaaccca cactgcagca gatcagccac   840
atcgcccagc agcttgggct cgagaaggat gtggtccgag tgtggttctg taaccggcgc  900
cagaagggca agcgatcaag cagcgactat gcacaacgag aggattttga ggctgctggg   960 tctccttct cagggggacc agtgtccttt cctctggccc cagggccca ttttggtacc   1020 ccaggctatg ggagccctca cttcactgca ctgtactcct cggtcccttt ccctgagggg  1080
gaagcctttc ccctgtctc cgtcaccact ctgggctctc ccatgcattc aaactgaggt   1140
gcctgccctt ctaggaatgg gggacagggg gaggggagga gctagggaaa gaaaacctgg   1200
agtttgtgcc agggttttg ggattaagtt cttcattcac taaggaagga attgggaaca   1260
caaagggtgg gggcagggga gtttgggca actggttgga gggaaggtga agttcaatga   1320
tgctcttgat tttaatccca catcatgtat cacttttttc ttaaataaag aagcctggga   1380
cacagtagat agacacactt aaaaaaaaa a                                    1411

<210> SEQ ID NO 2
<211> LENGTH: 360
<212> TYPE: PRT
<213> ORGANISM: Homo sapiens

<400> SEQUENCE: 2

Met Ala Gly His Leu Ala Ser Asp Phe Ala Phe Ser Pro Pro Pro Gly
1               5                   10                  15

Gly Gly Gly Asp Gly Pro Gly Gly Pro Glu Pro Gly Trp Val Asp Pro
                20                  25                  30

Arg Thr Trp Leu Ser Phe Gln Gly Pro Pro Gly Gly Pro Gly Ile Gly
            35                  40                  45

Pro Gly Val Gly Pro Gly Ser Glu Val Trp Gly Ile Pro Pro Cys Pro
    50                  55                  60

Pro Pro Tyr Glu Phe Cys Gly Gly Met Ala Tyr Cys Gly Pro Gln Val
65                  70                  75                  80

Gly Val Gly Leu Val Pro Gln Gly Gly Leu Glu Thr Ser Gln Pro Glu
                85                  90                  95

Gly Glu Ala Gly Val Gly Val Glu Ser Asn Ser Asp Gly Ala Ser Pro
            100                 105                 110

Glu Pro Cys Thr Val Thr Pro Gly Ala Val Lys Leu Glu Lys Glu Lys
        115                 120                 125

Leu Glu Gln Asn Pro Glu Glu Ser Gln Asp Ile Lys Ala Leu Gln Lys
    130                 135                 140

Glu Leu Glu Gln Phe Ala Lys Leu Leu Lys Gln Lys Arg Ile Thr Leu
145                 150                 155                 160

Gly Tyr Thr Gln Ala Asp Val Gly Leu Thr Leu Gly Val Leu Phe Gly
                165                 170                 175

Lys Val Phe Ser Gln Thr Thr Ile Cys Arg Phe Glu Ala Leu Gln Leu
            180                 185                 190

Ser Phe Lys Asn Met Cys Lys Leu Arg Pro Leu Leu Gln Lys Trp Val
        195                 200                 205
```

```
Glu Glu Ala Asp Asn Asn Glu Asn Leu Gln Glu Ile Cys Lys Ala Glu
    210                 215                 220

Thr Leu Val Gln Ala Arg Lys Arg Lys Arg Thr Ser Ile Glu Asn Arg
225                 230                 235                 240

Val Arg Gly Asn Leu Glu Asn Leu Phe Leu Gln Cys Pro Lys Pro Thr
                245                 250                 255

Leu Gln Gln Ile Ser His Ile Ala Gln Gln Leu Gly Leu Glu Lys Asp
            260                 265                 270

Val Val Arg Val Trp Phe Cys Asn Arg Arg Gln Lys Gly Lys Arg Ser
        275                 280                 285

Ser Ser Asp Tyr Ala Gln Arg Glu Asp Phe Glu Ala Ala Gly Ser Pro
290                 295                 300

Phe Ser Gly Gly Pro Val Ser Phe Pro Leu Ala Pro Gly Pro His Phe
305                 310                 315                 320

Gly Thr Pro Gly Tyr Gly Ser Pro His Phe Thr Ala Leu Tyr Ser Ser
                325                 330                 335

Val Pro Phe Pro Glu Gly Glu Ala Phe Pro Pro Val Ser Val Thr Thr
            340                 345                 350

Leu Gly Ser Pro Met His Ser Asn
            355                 360

<210> SEQ ID NO 3
<211> LENGTH: 2457
<212> TYPE: DNA
<213> ORGANISM: Homo sapiens

<400> SEQUENCE: 3
ctattaactt gttcaaaaaa gtatcaggag ttgtcaaggc agagaagaga gtgtttgcaa      60
aaagggaaaa gtactttgct gcctctttaa gactagggct gggagaaaga agaggagaga     120
gaaagaaagg agagaagttt ggagcccgag gcttaagcct tccaaaaac taatcacaac      180 aatcgcggcg gcccgaggag gagagcgcct gttttttcat cccaattgca cttcgcccgt     240
ctcgagctcc gcttcccccc aactattctc cgccagatct ccgcgcaggg ccgtgcacgc     300
cgaggccccc gcccgcggcc cctgcatccc ggccccgag cgcggccccc acagtcccgg      360
ccgggccgag ggttggcggc cgccggcggg ccgcgcccgc ccagcgcccg catgtataac     420
atgatggaga cggagctgaa gccgccgggc ccgcagcaag cttcgggggg cggcggcgga     480
ggaggcaacg ccacggcggc ggcgaccggc ggcaaccaga gaacagccc ggaccgcgtc      540 aagaggccca tgaacgcctt catggtatgg tcccgggggc agcggcgtaa gatggcccag     600
gagaacccca agatgcacaa ctcggagatc agcaagcgcc tgggcgcgga gtggaaactt     660
ttgtccgaga ccgagaagcg gccgttcatc gacgaggcca gcggctgcg cgctctgcac      720 atgaaggagc acccggatta taaataccgg ccgcggcgga aaaccaagac gctcatgaag     780
aaggataagt acacgcttcc cggaggcttg ctggccccg gcgggaacag catggcgagc      840
ggggttgggg tgggcgccgg cctgggtgcg ggcgtgaacc agcgcatgga cagctacgcg     900
cacatgaacg gctggagcaa cggcagctac agcatgatgc aggagcagct gggctacccg     960 cagcaccgg gcctcaacgc tcacggcgcg gcacagatgc aaccgatgca ccgctacgac    1020
gtcagcgccc tgcagtacaa ctccatgacc agctcgcaga cctacatgaa cggctcgccc    1080
acctacagca tgtcctactc gcagcagggc acccccggta tggcgctggg ctccatgggc    1140
tctgtggtca gtccgaggc cagctccagc cccccgtgg ttacctcttc ctcccactcc     1200
agggcgccct gccaggccgg ggacctccgg gacatgatca gcatgtacct ccccggcgcc    1260
```

```
gaggtgccgg agcccgctgc gcccagtaga ctgcacatgg cccagcacta ccagagcggc    1320
ccggtgcccg gcacggccat taacggcaca ctgcccctgt cgcacatgtg agggctggac    1380
tgcgaactgg agaaggggag agattttcaa agagatacaa gggaattggg aggggtgcaa    1440
aaagaggaga gtaggaaaaa tctgataatg ctcaaaagga aaaaaatct ccgcagcgaa      1500 acgacagctg cggaaaaaaa ccaccaatcc catccaaatt aacgcaaaaa ccgtgatgcc    1560
gactagaaaa cttttatgag agatcttggg acttcttttt gggggactat ttttgtacag    1620
agaaaacctg agggcggcgg ggagggcggg ggaatcggac catgtataga tctggaggaa    1680
aaaaactacg caaaactttt ttttaaagtt ctagtggtac gttaggcgct cgcagggag     1740 ttcgcaaaag tctttaccag taatatttag agctagactc cgggcgatga aaaaaagtt    1800 ttaatatttg caagcaactt ttgtacagta tttatcgaga taaacatggc aatcaaatgt    1860
ccattgttta aagctgaga atttgccaat attttttcgag gaaagggttc ttgctgggtt    1920
ttgattctgc agcttaaatt taggaccgtt acaaacaagg aaggagttta ttcggatttg    1980
aacattttag ttttaaaatt gtacaaaagg aaaacatgag agcaagtact ggcaagaccg    2040
ttttcgtggt cttgtttaag gcaaacgttc tagattgtac taaatttta acttactgtt     2100 aaaggcaaaa aaaaatgtc catgcaggtt gatatcgttg gtaatttata atagcttttg     2160
ttcaatccta ccctttcatt ttgttcacat aaaaatatg gaattactgt gtttgaaata    2220
ttttcttatg gtttgtaata tttctgtaaa ttgtgatatt ttaaggtttt tcccccctt      2280 tatttccgt agttgtattt taaaagattc ggctctgtta ttggaatcag gctgccgaga    2340
atccatgtat atatttgaac taataccatc cttataacag ctacattttc aacttaagtt    2400
tttactccat tatgcacagt ttgagataaa taaatttttg aaatatggac actgaaa       2457
```

<210> SEQ ID NO 4
<211> LENGTH: 317
<212> TYPE: PRT
<213> ORGANISM: Homo sapiens

<400> SEQUENCE: 4

```
Met Tyr Asn Met Met Glu Thr Glu Leu Lys Pro Gly Pro Gln Gln
1               5                   10                  15

Thr Ser Gly Gly Gly Gly Asn Ser Thr Ala Ala Ala Gly Gly
        20                  25                  30

Asn Gln Lys Asn Ser Pro Asp Arg Val Lys Arg Pro Met Asn Ala Phe
            35                  40                  45

Met Val Trp Ser Arg Gly Gln Arg Arg Lys Met Ala Gln Glu Asn Pro
    50                  55                  60

Lys Met His Asn Ser Glu Ile Ser Lys Arg Leu Gly Ala Glu Trp Lys
65                  70                  75                  80

Leu Leu Ser Glu Thr Glu Lys Arg Pro Phe Ile Asp Glu Ala Lys Arg
                85                  90                  95

Leu Arg Ala Leu His Met Lys Glu His Pro Asp Tyr Lys Tyr Arg Pro
            100                 105                 110

Arg Arg Lys Thr Lys Thr Leu Met Lys Lys Asp Lys Tyr Thr Leu Pro
        115                 120                 125

Gly Gly Leu Leu Ala Pro Gly Gly Asn Ser Met Ala Ser Gly Val Gly
    130                 135                 140

Val Gly Ala Gly Leu Gly Ala Gly Val Asn Gln Arg Met Asp Ser Tyr
145                 150                 155                 160
```

| | | | | | | | | | | | |
|---|---|---|---|---|---|---|---|---|---|---|---|
|Ala|His|Met|Asn|Gly|Trp|Ser|Asn|Gly|Ser|Tyr|Met|Met|Gln|Asp|
| | | |165| | | |170| | | |175| | | |

Gln Leu Gly Tyr Pro Gln His Pro Gly Leu Asn Ala His Gly Ala Ala
        180                 185               190

Gln Met Gln Pro Met His Arg Tyr Asp Val Ser Ala Leu Gln Tyr Asn
        195                 200               205

Ser Met Thr Ser Ser Gln Thr Tyr Met Asn Gly Ser Pro Thr Tyr Ser
        210                 215               220

Met Ser Tyr Ser Gln Gln Gly Thr Pro Gly Met Ala Leu Gly Ser Met
225               230               235               240

Gly Ser Val Val Lys Ser Glu Ala Ser Ser Ser Pro Pro Val Val Thr
        245                 250               255

Ser Ser Ser His Ser Arg Ala Pro Cys Gln Ala Gly Asp Leu Arg Asp
        260                 265               270

Met Ile Ser Met Tyr Leu Pro Gly Ala Glu Val Pro Glu Pro Ala Ala
        275                 280               285

Pro Ser Arg Leu His Met Ser Gln His Tyr Gln Ser Gly Pro Val Pro
        290                 295               300

Gly Thr Ala Ile Asn Gly Thr Leu Pro Leu Ser His Met
305               310               315

<210> SEQ ID NO 5
<211> LENGTH: 2949
<212> TYPE: DNA
<213> ORGANISM: Homo sapiens

<400> SEQUENCE: 5

```
agtttcccga ccagagagaa cgaacgtgtc tgcgggcgcg cggggagcag aggcggtggc      60
gggcggcggc ggcaccggga gccgccgagt gaccctcccc cgcccctctg gcccccacc     120 ctcccacccg cccgtggccc gcgcccatgg ccgcgcgcgc tccacacaac tcaccggagt    180
ccgcgccttg cgccgccgac cagttcgcag ctccgcgcca cggcagccag tctcacctgg    240
cggcaccgcc cgcccaccgc cccggccaca gccctgcgc ccacggcagc actcgaggcg     300
accgcgacag tggtggggga cgctgctgag tggaagagag cgcagcccgg ccaccggacc    360
tacttactcg ccttgctgat tgtctatttt tgcgtttaca acttttctaa gaacttttgt    420
atacaaagga acttttttaaa aaagacgctt ccaagttata tttaatccaa agaagaagga   480
tctcggccaa tttggggttt tgggttttgg cttcgtttct tctcttcgtt gactttgggg   540
ttcaggtgcc ccagctgctt cgggctgccg aggaccttct gggcccccac attaatgagg   600
cagccacctg gcgagtctga catggctgtc agcgacgcgc tgctcccatc tttctccacg   660
ttcgcgtctg gcccggcggg aagggagaag acactgcgtc aagcaggtgc cccgaataac   720
cgctggcggg aggagctctc ccacatgaag cgacttcccc cagtgcttcc cggccgcccc   780
tatgacctgg cggcggcgac cgtggccaca gacctggaga gcggcggagc cggtgcggct   840
tgcggcggta gcaacctggc gcccctacct cggagagaga ccgaggagtt caacgatctc   900
ctggacctgg actttattct ctccaattcg ctgacccatc ctccggagtc agtggccgcc   960
accgtgtcct cgtcagcgtc agcctcctct tcgtcgtcgc cgtcgagcag cggccctgcc  1020
agcgcgccct ccacctgcag cttcacctat ccgatccggg ccgggaacga cccgggcgtg  1080
gcgccgggcg gcacgggcgg aggcctcctc tatggcaggg agtccgctcc ccctccgacg  1140
gctcccttca acctggcgga catcaacgac gtgagccct cgggcggctt cgtgccgag    1200 ctcctgcggc cagaattgga cccggtgtac attccgccgc agcagccgca gccgccaggt  1260
```

```
ggcgggctga tgggcaagtt cgtgctgaag gcgtcgctga gcgcccctgg cagcgagtac   1320
ggcagcccgt cggtcatcag cgtcagcaaa ggcagccctg acggcagcca cccggtggtg   1380
gtggcgccct acaacggcgg gccgccgcgc acgtgcccca agatcaagca ggaggcggtc   1440
tcttcgtgca cccacttggg cgctggaccc cctctcagca atggccaccg gccggctgca   1500
cacgacttcc ccctggggcg gcagctcccc agcaggacta ccccgaccct gggtcttgag   1560
gaagtgctga gcagcaggga ctgtcaccct gccctgccgc ttcctcccgg cttccatccc   1620
cacccggggc ccaattaccc atccttcctg cccgatcaga tgcagccgca agtcccgccg   1680
ctccattacc aagagctcat gccacccggt tcctgcatgc cagaggagcc caagccaaag   1740
aggggaagac gatcgtggcc ccggaaaagg accgccaccc acacttgtga ttacgcgggc   1800
tgcggcaaaa cctacacaaa gagttcccat ctcaaggcac acctgcgaac ccacacaggt   1860
gagaaacctt accactgtga ctgggacggc tgtggatgga aattcgcccg ctcagatgaa   1920
ctgaccaggc actaccgtaa acacacgggg caccgcccgt tccagtgcca aaaatgcgac   1980
cgagcatttt ccaggtcgga ccacctcgcc ttacacatga gaggcatttt taaatccca   2040 gacagtggat atgacccaca ctgccagaag agaattcagt attttttact tttcacactg   2100
tcttcccgat gagggaagga gcccagccag aaagcactac aatcatggtc aagttcccaa   2160
ctgagtcatc ttgtgagtgg ataatcagga aaaatgagga atccaaaaga caaaaatcaa   2220
agaacagatg gggtctgtga ctggatcttc tatcattcca attctaaatc cgacttgaat   2280
attcctggac ttacaaaatg ccaaggggggt gactggaagt tgtggatatc agggtataaa   2340
ttatatccgt gagttggggg agggaagacc agaattccct tgaattgtgt attgatgcaa   2400
tataagcata aaagatcacc ttgtattctc tttaccttct aaaagccatt attatgatgt   2460
tagaagaaga ggaagaaatt caggtacaga aaacatgttt aaatagccta atgatggtg    2520 cttggtgagt cttggttcta aaggtaccaa acaaggaagc caaagttttc aaactgctgc   2580
atactttgac aaggaaaatc tatatttgtc ttccgatcaa catttatgac ctaagtcagg   2640
taatatacct ggtttacttc tttagcattt ttatgcagac agtctgttat gcactgtggt   2700
ttcagatgtg caataatttg tacaatggtt tattcccaag tatgccttaa gcagaacaaa   2760 tgtgttttc tatatagttc cttgccttaa taaatatgta atataaattt aagcaaacgt    2820
ctattttgta tatttgtaaa ctacaaagta aaatgaacat tttgtggagt ttgtatttg    2880 catactcaag gtgagaatta agttttaaat aaacctataa tatttatct gaaaaaaaaa    2940 aaaaaaaa                                                            2949
```

<210> SEQ ID NO 6
<211> LENGTH: 479
<212> TYPE: PRT
<213> ORGANISM: Homo sapiens

<400> SEQUENCE: 6

Met Arg Gln Pro Pro Gly Glu Ser Asp Met Ala Val Ser Asp Ala Leu
1               5                   10                  15

Leu Pro Ser Phe Ser Thr Phe Ala Ser Gly Pro Ala Gly Arg Glu Lys
            20                  25                  30

Thr Leu Arg Gln Ala Gly Ala Pro Asn Asn Arg Trp Arg Glu Glu Leu
        35                  40                  45

Ser His Met Lys Arg Leu Pro Pro Val Leu Pro Gly Arg Pro Tyr Asp
    50                  55                  60

-continued

```
Leu Ala Ala Ala Thr Val Ala Thr Asp Leu Glu Ser Gly Gly Ala Gly
65                  70                  75                  80

Ala Ala Cys Gly Gly Ser Asn Leu Ala Pro Leu Pro Arg Arg Glu Thr
                85                  90                  95

Glu Glu Phe Asn Asp Leu Leu Asp Leu Asp Phe Ile Leu Ser Asn Ser
            100                 105                 110

Leu Thr His Pro Pro Glu Ser Val Ala Ala Thr Val Ser Ser Ser Ala
            115                 120                 125

Ser Ala Ser Ser Ser Ser Pro Ser Ser Ser Gly Pro Ala Ser Ala
    130                 135                 140

Pro Ser Thr Cys Ser Phe Thr Tyr Pro Ile Arg Ala Gly Asn Asp Pro
145                 150                 155                 160

Gly Val Ala Pro Gly Gly Thr Gly Gly Gly Leu Leu Tyr Gly Arg Glu
                165                 170                 175

Ser Ala Pro Pro Pro Thr Ala Pro Phe Asn Leu Ala Asp Ile Asn Asp
            180                 185                 190

Val Ser Pro Ser Gly Gly Phe Val Ala Glu Leu Leu Arg Pro Glu Leu
            195                 200                 205

Asp Pro Val Tyr Ile Pro Pro Gln Gln Pro Gln Pro Pro Gly Gly Gly
    210                 215                 220

Leu Met Gly Lys Phe Val Leu Lys Ala Ser Leu Ser Ala Pro Gly Ser
225                 230                 235                 240

Glu Tyr Gly Ser Pro Ser Val Ile Ser Val Ser Lys Gly Ser Pro Asp
                245                 250                 255

Gly Ser His Pro Val Val Ala Pro Tyr Asn Gly Gly Pro Pro Arg
            260                 265                 270

Thr Cys Pro Lys Ile Lys Gln Glu Ala Val Ser Ser Cys Thr His Leu
    275                 280                 285

Gly Ala Gly Pro Pro Leu Ser Asn Gly His Arg Pro Ala Ala His Asp
    290                 295                 300

Phe Pro Leu Gly Arg Gln Leu Pro Ser Arg Thr Thr Pro Thr Leu Gly
305                 310                 315                 320

Leu Glu Glu Val Leu Ser Ser Arg Asp Cys His Pro Ala Leu Pro Leu
                325                 330                 335

Pro Pro Gly Phe His Pro His Pro Gly Pro Asn Tyr Pro Ser Phe Leu
            340                 345                 350

Pro Asp Gln Met Gln Pro Gln Val Pro Pro Leu His Tyr Gln Glu Leu
            355                 360                 365

Met Pro Pro Gly Ser Cys Met Pro Glu Glu Pro Lys Pro Lys Arg Gly
370                 375                 380

Arg Arg Ser Trp Pro Arg Lys Arg Thr Ala Thr His Thr Cys Asp Tyr
385                 390                 395                 400

Ala Gly Cys Gly Lys Thr Tyr Thr Lys Ser Ser His Leu Lys Ala His
                405                 410                 415

Leu Arg Thr His Thr Gly Glu Lys Pro Tyr His Cys Asp Trp Asp Gly
            420                 425                 430

Cys Gly Trp Lys Phe Ala Arg Ser Asp Glu Leu Thr Arg His Tyr Arg
            435                 440                 445

Lys His Thr Gly His Arg Pro Phe Gln Cys Gln Lys Cys Asp Arg Ala
    450                 455                 460

Phe Ser Arg Ser Asp His Leu Ala Leu His Met Lys Arg His Phe
465                 470                 475
```

```
<210> SEQ ID NO 7
<211> LENGTH: 2379
<212> TYPE: DNA
<213> ORGANISM: Homo sapiens

<400> SEQUENCE: 7 gaccccgag ctgtgctgct cgcggccgcc accgcgggc cccggccgtc cctggctccc      60
ctcctgcctc gagaagggca gggcttctca gaggcttggc gggaaaaaga acggagggag     120
ggatcgcgct gagtataaaa gccggttttc ggggctttat ctaactcgct gtagtaattc     180
cagcgagagg cagagggagc gagcgggcgg ccggctaggg tggaagagcc gggcgagcag     240
agctgcgctg cgggcgtcct gggaagggag atccggagcg aatagggggc ttcgcctctg     300
gcccagccct cccgctgatc ccccagccag cggtccgcaa cccttgccgc atccacgaaa     360 cttttgcccat agcagcgggc gggcactttg cactggaact acaacacccc gagcaaggac     420
gcgactctcc cgacgcgggg aggctattct gcccatttgg ggacacttcc ccgccgctgc     480
caggacccgc ttctctgaaa ggctctcctt gcagctgctt agacgctgga ttttttttcgg     540 gtagtggaaa accagcagcc tcccgcgacg atgcccctca cgttagcttt caccaacagg     600
aactatgacc tcgactacga ctcggtgcag ccgtatttct actgcgacga ggaggagaac     660
ttctaccagc agcagcagca gagcgagctg cagcccccgg cgcccagcga ggatatctgg     720
aagaaattcg agctgctgcc caccccgccc ctgtccccta gccgccgctc cgggctctgc     780
tcgccctcct acgttgcggt cacacccttc tcccttcggg gagacaacga cggcggtggc     840
gggagcttct ccacggccga ccagctggag atggtgaccg agctgctggg aggagacatg     900
gtgaaccaga gtttcatctg cgacccggac gacgagacct tcatcaaaaa catcatcatc     960
caggactgta tgtggagcgg cttctcggcc gccgccaagc tcgtctcaga aagctggcc     1020 tcctaccagg ctgcgcgcaa agacagcggc agcccgaacc ccgccgcgg ccacagcgtc    1080 tgctccacct ccagcttgta cctgcaggat ctgagcgccg ccgcctcaga gtgcatcgac    1140
ccctcggtgg tcttccccta ccctctcaac gacagcagct cgcccaagtc ctgcgcctcg    1200
caagactcca cgcgccttctc tccgtcctcg gattctctgc tctcctcgac ggagtcctcc    1260
ccgcagggca gccccgagcc cctggtgctc catgaggaga caccgccac caccagcagc    1320 gactctgagg aggaacaaga agatgaggaa gaaatcgatg ttgtttctgt ggaaaagagg    1380
caggctcctg gcaaaaggtc agagtctgga tcaccttctg ctggaggcca cagcaaacct    1440
cctcacagcc cactggtcct caagaggtgc cacgtctcca cacatcagca caactacgca    1500
gcgcctccct ccactcggaa ggactatcct gctgccaaga gggtcaagtt ggacagtgtc    1560
agagtcctga gacagatcag caacaaccga aaatgcacca gccccaggtc ctcggacacc    1620
gaggagaatg tcaagaggcg aacacacaac gtcttggagc gccagaggag gaacgagcta    1680
aaacggagct ttttgccct gcgtgaccag atcccggagt tggaaaacaa tgaaaaggcc    1740
cccaaggtag ttatccttaa aaaagccaca gcatacatcc tgtccgtcca agcagaggag    1800
caaaagctca tttctgaaga ggacttgttg cggaaacgac gagaacagtt gaaacacaaa    1860
cttgaacagc tacggaactc ttgtgcgtaa ggaaaagtaa ggaaaacgat tccttctaac    1920
agaaatgtcc tgagcaatca cctatgaact tgtttcaaat gcatgatcaa atgcaacctc    1980
acaaccttgg ctgagtcttg agactgaaag atttagccat aatgtaaact gcctcaaatt    2040
ggactttggg cataaaagaa cttttttatg cttaccatct ttttttttc tttaacagat    2100 ttgtatttaa gaattgtttt taaaaaattt taagatttac acaatgtttc tctgtaaata    2160
```

-continued

```
ttgccattaa atgtaaataa ctttaataaa acgtttatag cagttacaca gaatttcaat     2220
cctagtatat agtacctagt attataggta ctataaaccc taattttttt tatttaagta     2280
cattttgctt tttaaagttg attttttttct attgttttta gaaaaaataa aataactggc    2340
aaatatatca ttgagccaaa tcttaaaaaa aaaaaaaaa                            2379
```

<210> SEQ ID NO 8
<211> LENGTH: 454
<212> TYPE: PRT
<213> ORGANISM: Homo sapiens

<400> SEQUENCE: 8

```
Met Asp Phe Phe Arg Val Val Glu Asn Gln Gln Pro Pro Ala Thr Met
1               5                   10                  15

Pro Leu Asn Val Ser Phe Thr Asn Arg Asn Tyr Asp Leu Asp Tyr Asp
                20                  25                  30

Ser Val Gln Pro Tyr Phe Tyr Cys Asp Glu Glu Glu Asn Phe Tyr Gln
            35                  40                  45

Gln Gln Gln Gln Ser Glu Leu Gln Pro Pro Ala Pro Ser Glu Asp Ile
        50                  55                  60

Trp Lys Lys Phe Glu Leu Leu Pro Thr Pro Pro Leu Ser Pro Ser Arg
65                  70                  75                  80

Arg Ser Gly Leu Cys Ser Pro Ser Tyr Val Ala Val Thr Pro Phe Ser
                85                  90                  95

Leu Arg Gly Asp Asn Asp Gly Gly Gly Ser Phe Ser Thr Ala Asp
                100                 105                 110

Gln Leu Glu Met Val Thr Glu Leu Leu Gly Gly Asp Met Val Asn Gln
            115                 120                 125

Ser Phe Ile Cys Asp Pro Asp Asp Glu Thr Phe Ile Lys Asn Ile Ile
        130                 135                 140

Ile Gln Asp Cys Met Trp Ser Gly Phe Ser Ala Ala Lys Leu Val
145                 150                 155                 160

Ser Glu Lys Leu Ala Ser Tyr Gln Ala Ala Arg Lys Asp Ser Gly Ser
                165                 170                 175

Pro Asn Pro Ala Arg Gly His Ser Val Cys Ser Thr Ser Ser Leu Tyr
            180                 185                 190

Leu Gln Asp Leu Ser Ala Ala Ala Ser Glu Cys Ile Asp Pro Ser Val
        195                 200                 205

Val Phe Pro Tyr Pro Leu Asn Asp Ser Ser Ser Pro Lys Ser Cys Ala
    210                 215                 220

Ser Gln Asp Ser Ser Ala Phe Ser Pro Ser Ser Asp Ser Leu Leu Ser
225                 230                 235                 240

Ser Thr Glu Ser Ser Pro Gln Gly Ser Pro Glu Pro Leu Val Leu His
                245                 250                 255

Glu Glu Thr Pro Pro Thr Thr Ser Ser Asp Ser Glu Glu Glu Gln Glu
            260                 265                 270

Asp Glu Glu Glu Ile Asp Val Val Ser Val Glu Lys Arg Gln Ala Pro
        275                 280                 285

Gly Lys Arg Ser Glu Ser Gly Ser Pro Ser Ala Gly Gly His Ser Lys
    290                 295                 300

Pro Pro His Ser Pro Leu Val Leu Lys Arg Cys His Val Ser Thr His
305                 310                 315                 320

Gln His Asn Tyr Ala Ala Pro Pro Ser Thr Arg Lys Asp Tyr Pro Ala
                325                 330                 335
```

```
Ala Lys Arg Val Lys Leu Asp Ser Val Arg Val Leu Arg Gln Ile Ser
            340                 345                 350

Asn Asn Arg Lys Cys Thr Ser Pro Arg Ser Ser Asp Thr Glu Glu Asn
            355                 360                 365

Val Lys Arg Arg Thr His Asn Val Leu Glu Arg Gln Arg Arg Asn Glu
        370                 375                 380

Leu Lys Arg Ser Phe Phe Ala Leu Arg Asp Gln Ile Pro Glu Leu Glu
385                 390                 395                 400

Asn Asn Glu Lys Ala Pro Lys Val Val Ile Leu Lys Lys Ala Thr Ala
                405                 410                 415

Tyr Ile Leu Ser Val Gln Ala Glu Glu Gln Lys Leu Ile Ser Glu Glu
            420                 425                 430

Asp Leu Leu Arg Lys Arg Arg Glu Gln Leu Lys His Lys Leu Glu Gln
            435                 440                 445

Leu Arg Asn Ser Cys Ala
        450
```

<210> SEQ ID NO 9
<211> LENGTH: 2098
<212> TYPE: DNA
<213> ORGANISM: Homo sapiens

<400> SEQUENCE: 9

```
attataaatc tagagactcc aggattttaa cgttctgctg gactgagctg gttgcctcat      60
gttattatgc aggcaactca ctttatccca atttcttgat acttttcctt ctggaggtcc     120
tatttctcta acatcttcca gaaaagtctt aaagctgcct taaccttttt tccagtccac     180
ctcttaaatt ttttcctcct cttcctctat actaacatga gtgtggatcc agcttgtccc     240
caaagcttgc cttgctttga agcatccgac tgtaaagaat cttcacctat gcctgtgatt     300
tgtgggcctg aagaaaacta ccatccttg caaatgtctt ctgctgagat gcctcacacg      360
gagactgtct ctcctcttcc ttcctccatg gatctgctta tcaggacag ccctgattct      420
tccaccagtc ccaaaggcaa acaacccact tctgcagaga gagtgtcgc aaaaaaggaa      480
gacaaggtcc cggtcaagaa acagaagacc agaactgtgt tctcttccac ccagctgtgt    540
gtactcaatg atagatttca gagacagaaa tacctcagcc tccagcagat gcaagaactc    600
tccaacatcc tgaacctcag ctacaaacag gtgaagacct ggttccagaa ccagagaatg    660
aaatctaaga ggtggcagaa aaacaactgg ccgaagaata gcaatggtgt gacgcagaag    720
gcctcagcac ctacctaccc cagcctttac tcttcctacc accagggatg cctggtgaac    780
ccgactggga accttccaat gtggagcaac cagacctgga caattcaac ctggagcaac     840
cagacccaga acatccagtc ctggagcaac cactcctgga acactcagac ctggtgcacc    900
caatcctgga caatcaggc ctggaacagt cccttctata actgtggaga ggaatctctg      960
cagtcctgca tgcagttcca gccaaattct cctgccagtg acttggaggc tgccttggaa   1020
gctgctgggg aaggccttaa tgtaatacag cagaccacta ggtatttag tactccacaa    1080
accatggatt tattcctaaa ctactccatg aacatgcaac ctgaagacgt gtgaagatga   1140
gtgaaactga tattactcaa tttcagtctg gacactggct gaatccttcc tctccctcc    1200
tcccatccct cataggattt tcttgtttg gaaaccacgt gttctggttt ccatgatgcc    1260
catccagtca atctcatgga gggtggagta tggttggagc ctaatcagcg aggtttcttt   1320
tttttttttt ttcctattgg atcttcctgg agaaaatact ttttttttt ttttttttga    1380
aacggagtct tgctctgtcg cccaggctgg agtgcagtgg cgcggtcttg gctcactgca   1440
```

-continued

```
agctccgtct cccgggttca cgccattctc ctgcctcagc ctcccgagca gctgggacta    1500
caggcgcccg ccacctcgcc cggctaatat tttgtatttt tagtagagac ggggtttcac    1560
tgtgttagcc aggatggtct cgatctcctg accttgtgat ccacccgcct cggcctccct    1620
aacagctggg atttacaggc gtgagccacc gcgccctgcc tagaaaagac attttaataa    1680
ccttggctgc cgtctctggc tatagataag tagatctaat actagtttgg atatctttag    1740
ggtttagaat ctaacctcaa gaataagaaa tacaagtaca aattggtgat gaagatgtat    1800
tcgtattgtt tgggattggg aggctttgct tatttttaa aaactattga ggtaaagggt     1860
taagctgtaa catacttaat tgatttctta ccgttttgg ctctgttttg ctatatcccc     1920
taatttgttg gttgtgctaa tctttgtaga aagaggtctc gtatttgctg catcgtaatg    1980
acatgagtac tgctttagtt ggtttaagtt caaatgaatg aaacaactat ttttccttta    2040
gttgatttta ccctgatttc accgagtgtt tcaatgagta aatatacagc ttaaacat     2098
```

<210> SEQ ID NO 10
<211> LENGTH: 305
<212> TYPE: PRT
<213> ORGANISM: Homo sapiens

<400> SEQUENCE: 10

```
Met Ser Val Asp Pro Ala Cys Pro Gln Ser Leu Pro Cys Phe Glu Ala
1               5                   10                  15

Ser Asp Cys Lys Glu Ser Ser Pro Met Pro Val Ile Cys Gly Pro Glu
            20                  25                  30

Glu Asn Tyr Pro Ser Leu Gln Met Ser Ser Ala Glu Met Pro His Thr
        35                  40                  45

Glu Thr Val Ser Pro Leu Pro Ser Ser Met Asp Leu Leu Ile Gln Asp
    50                  55                  60

Ser Pro Asp Ser Ser Thr Ser Pro Lys Gly Lys Gln Pro Thr Ser Ala
65                  70                  75                  80

Glu Lys Ser Val Ala Lys Lys Glu Asp Lys Val Pro Val Lys Lys Gln
                85                  90                  95

Lys Thr Arg Thr Val Phe Ser Thr Gln Leu Cys Val Leu Asn Asp
            100                 105                 110

Arg Phe Gln Arg Gln Lys Tyr Leu Ser Leu Gln Gln Met Gln Glu Leu
        115                 120                 125

Ser Asn Ile Leu Asn Leu Ser Tyr Lys Gln Val Lys Thr Trp Phe Gln
    130                 135                 140

Asn Gln Arg Met Lys Ser Lys Arg Trp Gln Lys Asn Asn Trp Pro Lys
145                 150                 155                 160

Asn Ser Asn Gly Val Thr Gln Lys Ala Ser Ala Pro Thr Tyr Pro Ser
                165                 170                 175

Leu Tyr Ser Ser Tyr His Gln Gly Cys Leu Val Asn Pro Thr Gly Asn
            180                 185                 190

Leu Pro Met Trp Ser Asn Gln Thr Trp Asn Asn Ser Thr Trp Ser Asn
        195                 200                 205

Gln Thr Gln Asn Ile Gln Ser Trp Ser Asn His Ser Trp Asn Thr Gln
    210                 215                 220

Thr Trp Cys Thr Gln Ser Trp Asn Asn Gln Ala Trp Asn Ser Pro Phe
225                 230                 235                 240

Tyr Asn Cys Gly Glu Glu Ser Leu Gln Ser Cys Met Gln Phe Gln Pro
                245                 250                 255
```

```
Asn Ser Pro Ala Ser Asp Leu Glu Ala Ala Leu Glu Ala Ala Gly Glu
                260                 265                 270

Gly Leu Asn Val Ile Gln Gln Thr Thr Arg Tyr Phe Ser Thr Pro Gln
            275                 280                 285

Thr Met Asp Leu Phe Leu Asn Tyr Ser Met Asn Met Gln Pro Glu Asp
    290                 295                 300

Val
305

<210> SEQ ID NO 11
<211> LENGTH: 4014
<212> TYPE: DNA
<213> ORGANISM: Homo sapiens

<400> SEQUENCE: 11
```

| | | | | | |
|---|---|---|---|---|---|
| gtgcggggga | agatgtagca | gcttcttctc | cgaaccaacc | ctttgccttc | ggacttctcc | 60 |
| ggggccagca | gccgcccgac | caggggcccg | ggccacggg | ctcagccgac | gaccatgggc | 120 |
| tccgtgtcca | accagcagtt | tgcaggtggc | tgcgccaagg | cggcagaaga | ggcgcccgag | 180 |
| gaggcgccgg | aggacgcggc | ccgggcggcg | gacgagcctc | agctgctgca | cggtgcgggc | 240 |
| atctgtaagt | ggttcaacgt | gcgcatgggg | ttcggcttcc | tgtccatgac | cgcccgcgcc | 300 |
| ggggtcgcgc | tcgaccccc | agtggatgtc | tttgtgcacc | agagtaagct | gcacatggaa | 360 |
| gggttccgga | gcttgaagga | gggtgaggca | gtggagttca | cctttaagaa | gtcagccaag | 420 |
| ggtctggaat | ccatccgtgt | caccggacct | ggtggagtat | tctgtattgg | gagtgagagg | 480 |
| cggccaaaag | gaaagagcat | gcagaagcgc | agatcaaaag | gagacaggtg | ctacaactgt | 540 |
| ggaggtctag | atcatcatgc | caaggaatgc | aagctgccac | cccagcccaa | gaagtgccac | 600 |
| ttctgccaga | gcatcagcca | tatggtagcc | tcatgtccgc | tgaaggccca | gcagggccct | 660 |
| agtgcacagg | gaaagccaac | ctactttcga | gaggaagaag | aagaaatcca | cagccctacc | 720 |
| ctgctccccgg | aggcacagaa | ttgagccaca | atgggtgggg | gctattcttt | tgctatcagg | 780 |
| aagttttgag | gagcaggcag | agtggagaaa | gtgggaatag | ggtgcattgg | ggctagttgg | 840 |
| cactgccatg | tatctcaggc | ttgggttcac | accatcaccc | tttcttccct | ctaggtgggg | 900 |
| ggaaagggtg | agtcaaagga | actccaacca | tgctctgtcc | aaatgcaagt | gagggttctg | 960 |
| ggggcaacca | ggaggggga | atcaccctac | aacctgcata | ctttgagtct | ccatccccag | 1020 |
| aatttccagc | ttttgaaagt | ggcctggata | gggaagttgt | tttccttta | aagaaggata | 1080 |
| tataataatt | cccatgccag | agtgaaatga | ttaagtataa | gaccagattc | atggagccaa | 1140 |
| gccactacat | tctgtggaag | gagatctctc | aggagtaagc | attgtttttt | tttcacatct | 1200 |
| tgtatcctca | tacccacttt | tgggataggg | tgctggcagc | tgtcccaagc | aatgggtaat | 1260 |
| gatgatggca | aaaagggtgt | tgggggaac | agctgcagac | ctgctgctct | atgctcaccc | 1320 |
| ccgcccatt | ctgggccaat | gtgattttat | ttatttgctc | ccttggatac | tgcaccttgg | 1380 |
| gtcccacttt | ctccaggatg | ccaactgcac | tagctgtgtg | cgaatgacgt | atcttgtgca | 1440 |
| ttttaacttt | ttttccttaa | tataaatatt | ctggttttgt | attttttgtat | attttaatct | 1500 |
| aaggccctca | tttcctgcac | tgtgttctca | ggtacatgag | caatctcagg | gatagccagc | 1560 |
| agcagctcca | ggtctgcgca | gcaggaatta | cttttttgttg | ttttttgccac | cgtggagagc | 1620 |
| aactatttgg | agtgcacagc | ctattgaact | acctcatttt | tgccaataag | agctggcttt | 1680 |
| tctgccatag | tgtcctcttg | aaaccccctc | tgccttgaaa | atgttttatg | ggagactagg | 1740 |
| ttttaactgg | gtggccccat | gacttgattg | ccttctactg | gaagattggg | aattagtcta | 1800 |

```
aacaggaaat ggtggtacac agaggctagg agaggctggg cccggtgaaa aggccagaga    1860
gcaagccaag attaggtgag ggttgtctaa tcctatggca caggacgtgc tttacatctc    1920
cagatctgtt cttcaccaga ttaggttagg cctaccatgt gccacagggt gtgtgtgtgt    1980
ttgtaaaact agagttgcta aggataagtt taaagaccaa tacccctgta cttaatcctg    2040
tgctgtcgag ggatggatat atgaagtaag gtgagatcct taaccttcca aaattttcgg    2100
gttccaggga gacacacaag cgagggtttt gtggtgcctg gagcctgtgt cctgccctgc    2160
tacagtagtg attaatagtg tcatggtagc taaaggagaa aaaggggggtt tcgtttacac    2220 gctgtgagat caccgcaaac ctaccttact gtgttgaaac gggacaaatg caatagaacg    2280
cattgggtgg tgtgtgtctg atcctgggtt cttgtctccc ctaaatgctg cccccccaagt    2340 tactgtattt gtctgggctt tgtaggactt cactacgttg attgctaggt ggcctagttt    2400
gtgtaaatat aatgtattgg tctttctccg tgttctttgg gggttttgtt tacaaacttc    2460 ttttttgtatt gagagaaaaa tagccaaagc atctttgaca gaaggttctg caccaggcaa    2520
aaagatctga acattagtt tgggggggccc tcttcttaaa gtggggatct tgaaccatcc    2580
tttcttttgt attccccttc ccctattacc tattagacca gatcttctgt cctaaaaact    2640
tgtcttctac cctgccctct tttctgttca cccccaaaag aaaacttaca cacccacaca    2700
catacacatt tcatgcttgg agtgtctcca caactcttaa atgatgtatg caaaaatact    2760
gaagctagga aaaccctcca tcccttgttc ccaacctcct aagtcaagac cattaccatt    2820
tctttctttc tttttttttt tttttaaaa tgggagtctca ctgtgtcacc caggctggag    2880
tgcagtggca tgatcggctc actgcagcct ctgcctcttg ggttcaagtg attctcctgc    2940
ctcagcctcc tgagtagctg ggatttcagg caccgccac actcagctaa ttttttgtatt    3000 ttagtagag acggggtttc accatgttgt ccaggctggt ctggaactcc tgacctcagg    3060
tgatctgccc accttggctt cccaaagtgc tgggattaca ggcatgagcc accatgctgg    3120
gccaaccatt tcttggtgta ttcatgccaa acacttaaga cactgctgta gcccaggcgc    3180
ggtggctcac acctgtaatc ccagcacttt ggaaggctga ggcgggcgga tcacaaggtc    3240
acgagttcaa aactatcctg gccaacacag tgaaaccccg tctctactaa aatacaaaaa    3300
aattagccgg gtgtggtggt gcatgccttt agtcctagct attcaggagg ctgaggcagg    3360
ggaatcgctt gaacccgaga ggcagaggtt gcagtgagct gagatcgcac cactgcactc    3420
cagcctggtt acagagcaag actctgtctc aaacaaaaca aaacaaaaca aaacacact    3480 actgtatttt ggatggatca aacctcctta atttttaattt ctaatcctaa agtaaagaga    3540
tgcaattggg ggccttccat gtagaaagtg gggtcaggag gccaagaaag ggaatatgaa    3600
tgtatatcca agtcactcag gaactttat gcaggtgcta gaaactttat gtcaaagtgg    3660
ccacaagatt gtttaatagg agacgaacga atgtaactcc atgttactg ctaaaaacca    3720 aagctttgtg taaatcttg aatttatggg gcggagggt aggaaagcct gtacctgtct    3780 gttttttttcc tgatccttttt ccctcattcc tgaactgcag gagactgagc ccctttgggc    3840
tttggtgacc ccatcactgg ggtgtgttta tttgatggtt gattttgctg tactgggtac    3900
ttcctttccc atttctaat cattttttaa cacaagctga ctcttccctt cccttctcct    3960
ttccctggga aaatacaatg aataaataaa gacttattgg tacgcaaact gtca    4014

<210> SEQ ID NO 12
<211> LENGTH: 209
<212> TYPE: PRT
```

```
<213> ORGANISM: Homo sapiens

<400> SEQUENCE: 12

Met Gly Ser Val Ser Asn Gln Gln Phe Ala Gly Gly Cys Ala Lys Ala
1               5                   10                  15

Ala Glu Glu Ala Pro Glu Glu Ala Pro Glu Asp Ala Ala Arg Ala Ala
            20                  25                  30

Asp Glu Pro Gln Leu Leu His Gly Ala Gly Ile Cys Lys Trp Phe Asn
        35                  40                  45

Val Arg Met Gly Phe Gly Phe Leu Ser Met Thr Ala Arg Ala Gly Val
    50                  55                  60

Ala Leu Asp Pro Pro Val Asp Val Phe Val His Gln Ser Lys Leu His
65                  70                  75                  80

Met Glu Gly Phe Arg Ser Leu Lys Glu Gly Glu Ala Val Glu Phe Thr
                85                  90                  95

Phe Lys Lys Ser Ala Lys Gly Leu Glu Ser Ile Arg Val Thr Gly Pro
            100                 105                 110

Gly Gly Val Phe Cys Ile Gly Ser Glu Arg Arg Pro Lys Gly Lys Ser
        115                 120                 125

Met Gln Lys Arg Arg Ser Lys Gly Asp Arg Cys Tyr Asn Cys Gly Gly
    130                 135                 140

Leu Asp His His Ala Lys Glu Cys Lys Leu Pro Pro Gln Pro Lys Lys
145                 150                 155                 160

Cys His Phe Cys Gln Ser Ile Ser His Met Val Ala Ser Cys Pro Leu
                165                 170                 175

Lys Ala Gln Gln Gly Pro Ser Ala Gln Gly Lys Pro Thr Tyr Phe Arg
            180                 185                 190

Glu Glu Glu Glu Glu Ile His Ser Pro Thr Leu Leu Pro Glu Ala Gln
        195                 200                 205

Asn
```

METHOD FOR REJUVENATING CELLS

FIELD OF THE INVENTION

The invention relates to a method for reprogramming cells from aged donors or senescent cells to pluripotent cells that have lost marks of senescence. In particular, the invention relates to an ex vivo method for preparing induced pluripotent stem cells (iPSCs) from a target cell population from aged donors or senescent cells, said method comprising the steps of culturing said target cell population under appropriate conditions for reprogramming said cells into iPSCs, wherein said appropriate conditions comprises increasing expression in said target cells, of at least the following combination of reprogramming factors: Oct4, Klf4, Sox2, c-Myc, Lin28 and, optionally Nanog.

BACKGROUND OF THE INVENTION

The discovery of induced Pluripotent Stem Cells (iPSCs) by S. Yamanaka[1,2], and very rapid progress in iPSC technology have opened up a new avenue in autologous regenerative medicine, whereby patient-specific pluripotent cells could potentially be derived from adult somatic cells. iPSCs have been reproducibly obtained in different cell types by forced expression of the OCT4, SOX2, c-MYC and KLF4 transcription factor cocktail or by an alternative combination of factors, substituting KLF4 and c-MYC by NANOG and LIN28[3].

Cellular senescence is linked to physiological aging, and is characterized by a stable cell cycle arrest in response to various forms of stress stimuli, including oncogene activation or extremely shortened telomeres called replicative senescence[9,10]. A common feature is the activation of the p53/p21$^{CIP1}$ and pRb/p16$^{INK4A}$ tumor suppressor pathways in these cells, associated with alteration of morphology, increase in senescence-associated β-galactosidase (SA-β-Gal) activity, a specific SA secretome (SASP) and formation of senescence-associated heterochromatic foci (SAHF), which are thought to be involved in repression of genes that promote cell division[11].

EP 2 096 169 discloses a process for generating induced pluripotent stem cells from somatic cells, comprising the step of introducing the following six genes: Oct family gene, Klf family gene, Sox family gene, Myc family gene, Lin28 and Nanog into somatic cells. However, this specific combination of reprogramming factors has never been applied to senescent cells or cells from aged donors.

It has been recently described by several groups, that cellular senescence is a barrier to reprogramming, due to up-regulation of p53, p16$^{INK4A}$, and p21$^{CIP1}$, suggesting that cellular aging might be an important limitation of this technology. Accordingly, ablation of different senescence effectors has been proposed as a potential solution to improve the efficiency of iPSCs generation[4-8].

WO 2011/016588 suggests using functional inhibitors of p53 together with a cocktail of reprogramming factors consisting of Oct3/4, Sox2, Klf4, L-myc and Lin28. p53 shRNA were used as functional inhibitors of p53.

The inventors have now shown that using the specific combination of the six factors OCT4, NANOG, SOX2, KLF4, c-MYC and LIN28 allows efficient reprogramming of both proliferative centenarian and senescent fibroblasts into human iPSCs, without the need of ablating senescence effectors, contrary to the technical prejudice in the art related to reprogramming of senescent cells.

Moreover, the inventors showed that this reprogramming restores telomere size, gene expression profile, oxidative stress and mitochondrial metabolism as observed in human embryonic stem cells (hESCs). Surprisingly, iPSCs derived from aged and senescent cells do not retain detectable marks of the cellular aging phenotype, and are indistinguishable from hESCs. Finally, iPSCs re-differentiated into fibroblasts exhibit an increased potential to proliferate, and gene expression profile equivalent to young proliferative fibroblasts, demonstrating that the reprogramming strategy according to the present invention erases the hallmarks of the cellular aging phenotype, defining a new method to produce rejuvenated cells.

To the applicant's knowledge, the invention is the first description of a method for producing iPSCs with cells from aged donors or senescent cells, therefore the invention may be highly useful in particular in autologous regenerative medicine, whereby patient-specific pluripotent cells could potentially be derived from adult aged or senescent somatic cells, and will also find numerous applications in the research field. Moreover, the invention is useful as a general method to rejuvenating senescent cells or cells from aged donors, either in vitro or in vivo.

SUMMARY OF THE INVENTION

A first aspect of the invention relates to an ex vivo method for preparing induced pluripotent stem cells (iPSCs) from a target cell population comprising cells from aged donors or senescent cells or cells overexpressing p16$^{INK4A}$ or p21$^{CIP}$ senescence effectors, said method comprising the steps of:
  a) providing said target cell population comprising cells from aged donors or senescent cells or cells overexpressing p16$^{INK4A}$ or p21$^{CIP}$ senescence effectors, and,
  b) culturing said target cell population under appropriate conditions for reprogramming said target cell population into iPSCs, wherein said appropriate conditions comprises increasing expression in said target cell population of at least the following combination of reprogramming factors:
  i. a reprogramming factor encoded by one gene of the Oct family gene,
  ii. a reprogramming factor encoded by one gene of the Klf family gene,
  iii. a reprogramming factor encoded by one gene of the Sox family gene,
  iv. a reprogramming factor encoded by one gene of the Myc family gene, and
  v. Lin28,
  vi. and, optionally, Nanog.

In a preferred embodiment, said appropriate conditions comprise increasing expression in said target cell population of the following reprogramming factors: Oct4, Klf4, Sox2, c-Myc (or L-myc), Lin28 and, optionally Nanog. In a related embodiment, said appropriate conditions comprise increasing expression in said target cell population of the following reprogramming factors: Oct4, Klf4, Sox2, c-Myc (or L-myc), Lin28 and Nanog.

The inventors have shown that marks of senescence can be fully erased by the method of the invention. Thus, advantageously, the target cell population may be selected from cell population comprising adult somatic cells from aged donors or senescent cells such as senescent fibroblasts, or from any kind of cells harboring aged or senescent associated physiology, like premature aging syndrome. In one specific embodiment, the target cell population is a human cell population obtained from an adult subject being at least 50 years old, with apparently no limits in aged as a 101 years old donor cell population was efficiently reprogrammed with this strategy, for example at least 60, 70, 80, 90, or 100 years old, for example in need of regenerative autologous cell therapy.

Advantageously, the method may not comprise any step of direct silencing of senescence effectors, such as $p21^{CIP1}$ and/or $p16^{INK4a}$ and or p53. In particular, the method may not comprise any use of functional inhibitors of p53, such as p53 shRNA.

In one embodiment, conditions for increasing expression of the reprogramming factors listed above comprise either
  (a) introducing one or more expression vectors comprising the coding sequences of said reprogramming factors; or,
  (b) directly delivering an effective amount of each reprogramming factor or their precursor RNA,
  into said target cell population.

In one specific embodiment, the method of the invention comprises the step of transfecting said target cell population with a combination of viral vectors, each viral vector comprising the coding sequence of each of the reprogramming factors, Oct4, Klf4, Sox2, c-Myc (or L-myc), Lin28 and, optionally, Nanog.

The invention further relates to the induced pluripotent stem cells obtainable by the method described above, in particular to induced pluripotent stem cells obtainable by the method and obtained from aged or senescent cells.

The invention further relates to an in vitro method for rejuvenating cells from aged donors or senescent cells comprising reprogramming said cells from aged donors or senescent cells to induced pluripotent stem cells, by increasing expression in said cells from aged donors or senescent cells of at least a combination of the following reprogramming factors:
  i. a reprogramming factor encoded by one gene of the Oct family gene,
  ii. a reprogramming factor encoded by one gene of the Klf family gene,
  iii. a reprogramming factor encoded by one gene of the Sox family gene,
  iv. a reprogramming factor encoded by one gene of the Myc family gene, and,
  v. Lin28,
  vi. and, optionally, Nanog.

The invention further relates to a composition for in vivo use in rejuvenating cells from aged donors or senescent cells in a subject in need thereof, said composition comprising means for increasing expression of the following reprogramming factors Oct4, Klf4, Sox2, c-Myc, Lin28 and, optionally, Nanog into said aged or senescent cells.

In one embodiment, said means for increasing expression of said reprogramming factors comprise a combination of Oct4 protein, Klf4 protein, Sox2 protein, c-Myc protein, Lin28 protein and, optionally, Nanog protein, wherein each protein is associated to appropriate means for delivery of said protein into the nucleus of the cells to be rejuvenated.

Alternatively, said means for increasing expression of said reprogramming factors may comprise a combination of Oct4 precursor RNA, Klf4 precursor RNA, Sox2 precursor RNA, c-Myc precursor RNA, Lin28 precursor RNA and, optionally, Nanog precursor RNA, wherein each precursor RNA is associated to appropriate means for delivery of each precursor RNA into the cytoplasm of the cells to be rejuvenated.

The compositions of the invention as described above may advantageously be suitable for topical application.

DETAILED DESCRIPTION OF THE INVENTION

A first aspect of the invention relates to an ex vivo method for preparing induced pluripotent stem cells (iPSCs) from a target cell population comprising cells from aged donors or senescent cells or cells overexpressing $p16^{INK4A}$ or $p21^{CIP}$ senescence effectors, said method comprising the steps of:
  a) providing said target cell population comprising cells from aged donors or senescent cells or cells overexpressing $p16^{INK4A}$ or $p21^{CIP}$ senescence effectors, and,
  b) culturing said target cell population under appropriate conditions for reprogramming said target cell population into iPSCs, wherein said appropriate conditions comprises increasing expression in said target cell population, of at least the following combination of reprogramming factors:
    i. a reprogramming factor encoded by one gene of the Oct family gene,
    ii. a reprogramming factor encoded by one gene of the Klf family gene,
    iii. a reprogramming factor encoded by one gene of the Sox family gene,
    iv. a reprogramming factor encoded by one gene of the Myc family gene, and,
    v. Lin28, and, optionally,
    vi. Nanog.

As used herein, the term "pluripotent" refers to cells with the ability to give rise to progeny that can undergo differentiation, under appropriate conditions, into cell types that collectively exhibit characteristics associated with cell lineages from the three germ layers (endoderm, mesoderm, and ectoderm). Pluripotent stem cells can contribute to tissues of a prenatal, postnatal or adult organism. A standard art-accepted test, such as the ability to form a teratoma in 8-12 week old SCID mice, can be used to establish the pluripotency of a cell population. However, identification of various pluripotent stem cell characteristics can also be used to identify pluripotent cells.

More specifically, human pluripotent stem cells may express at least some, and optionally all, of the markers from the following non-limiting list: SSEA-3, SSEA-4, TRA-1-60, TRA-1-81, TRA-2-49/6E, ALP, Sox2, E-cadherin, UTF-I, Oct4, Lin28, Rex1, and Nanog.

As used herein, the term "induced pluripotent stem cell" refers to a pluripotent stem cell artificially derived from a non-pluripotent cell. A non-pluripotent cell can be a cell of lesser potency to self-renew and differentiate than a pluripotent stem cell. Cells of lesser potency can be, but are not limited to, somatic stem cells, tissue specific progenitor cells, primary or secondary cells. One remarkable advantage of the present method is that it enables the production of induced pluripotent stem cells from any somatic cells, including aged or senescent cells, previously believed as non inducible to pluripotency due to their aging phenotype.

The term "reprogramming" refers to the process of changing the fate of a target cell into that of a different cell type, caused by the expression of a small set of factors (or reprogramming factors) in the target cells. For example, methods for reprogramming fibroblast cells to induced pluripotent stem cells by expressing ectopically Oct3/4, Sox2, c-myc and Klf4 have been described by Takahashi and Yamanaka, 2006[1].

Accordingly, a "reprogramming factor" is a factor, for example, it may be a transcription factor, which can be used to reprogram a target cell. The term "reprogramming factor"

further includes any analogue molecule that mimics the function of the factor with respect to reprogramming capacity.

The Target Cell Population for Use in the Method of the Invention

The target cell population for use in the method of the present invention is advantageously a cell population comprising either cells from aged donors or senescent cells or cells overexpressing $p16^{INK4A}$ or $p21^{CIP}$ senescence effectors. These cells may be obtained from living of frozen tissues of animals.

The term "senescent cells" refers to cells that exhibit cell cycle arrest, generally during the G1 transition of the cell cycle or in few cases in G2, elicited by replicative exhaustion due to telomere attrition or in response to stresses such as DNA damage, chemotherapeutic drugs, or aberrant expression of oncogenes. This arrest is implemented primarily through activation of p53 and the up-regulation of the cyclin-dependent kinase (CDK) inhibitors $p16^{INK4a}$ and $p21^{CIP1}$ (Collado et al. 2007, Cell, 130: 223-233).

"Senescent cells" may be characterized by at least one or more of the following characteristics:
- activation of the $p53/p21^{CIP1}$ and $pRb/p16^{INK4A}$ tumor suppressor pathways (hereafter referred as senescence effectors),
- cells arrested irreversibly in G1,
- shortening of telomere size,
- expression of senescent-associated β-galactosidase activity (SA β-Gal),
- Specific chromatin modification as senescence-associated heterochromatic foci (SAHF),
- Specific secretome,
- reduced/altered overall mitochondrial activity.

Irreversible cell arrest in G1 may be assessed by FACS as described in Matsuura et al[25] and briefly summarized below:

To analyze the cell cycle, trypsinized cells are fixed with cooled 70% EtOH during at least 15 min at 4° C. Fixed cells are centrifuged and resuspended in PBS before staining with Propidium Iodide (10 µg/ml) plus RNase A (250 µg/ml) during 30 min and analysis by flow cytometry, using for example a FacsCalibur II (BD Biosciences).

Shortening of telomere size may be characterized by evaluating the mean terminal restriction fragment (TRF) length for example by Southern blot analysis, for example as described in the Examples below.

A method for detecting expression of senescent-associated β-galactosidase activity (SA β-Gal) is described in Matsuura et al[25] and briefly summarized below:

Cell cultures are stained as described (Dimri et al. Proc Natl Acad Sci USA. 1995 Sep. 26; 92(20):9363-7). Briefly, cells are washed with phosphate-buffered saline (PBS) and fixed with 1% paraformaldehyde for 3 minutes at room-vtemperature, then washed three times with PBS for 5 minutes each at room temperature. Staining is performed overnight in a non-CO2 enriched incubator at 37° C. using a solution pH 6 containing 40 mM sodium phosphate (dibasic), 40 mM citric acid, 150 mM NaCl, 2 mM MgCl2, 5 mM potassium ferrocyanide, 5 mM potassium ferricyanide, 1 mg/ml X-gal (5-bromo-4-chloro-3-indolyl-b-D-galactoside, Pierce Chemical Co., Rockford, Ill.). Cyanide salts and X-gal are added from freshly made 100 X_stocks in PBS and dimethylformamide, respectively. Cells are then washed three times with PBS for 5 minutes each at room temperature, before microscopic examination and photography.

A method for detecting expression of senescence-associated heterochromatic foci (SAHF) by indirect immunofluorescence is described in the Examples below.

Overall mitochondrial activity can be evaluated by measuring the transmembrane potential generated by the proton gradient. A method for measuring this parameter using the cationic dye JC-1 is for example described in the Examples below.

Cells from aged donors comprise a number of proliferative cells that exhibit certain characteristics of senescent cells, in particular
- upregulation of the tumor suppressors $p16^{INK4a}$ and $p21^{CIP1}$ (hereafter referred as senescence effectors).
- decreased ability to proliferate,
- global genome CpG hypomethylation,
- unscheduled heterochromatinization.

Upregulation of the tumor suppressors $p16^{INK4a}$ and $p21^{CIP1}$ can be observed using usual techniques in the Art for measuring protein expression and/or mRNA expression, for example, Western Blot, Northern Blot or Real-Time PCR. Upregulation is observed when significant higher expression of $p16^{INK4a}$ and $p21^{CIP1}$ is observed in the test cells compared to controlled (non senescent) cells, for example embryonic stem cells.

The inventors have shown that proliferative and senescent cells from aged donors (more than 70 years old) have a different signature, for example in terms of gene expression or metabolism, from cells of young donors. The iPSCs obtained according to the method have a signature that is closer to the embryonic stem cells and distinguish in that respect with iPSCs obtained with the conventional cocktail of 4 reprogramming factors OCT4, SOX2, c-MYC and KLF4.

To applicant's knowledge, the method of the invention comprising the use of a combination of at least 5, preferably 6 specific reprogramming factors is the only method described in the art for generating induced pluripotent stem cells from senescent cells or cells of aged donors. Accordingly, the method of the invention is particularly useful for cell population susceptible to contain senescent cells in a high proportion.

In one preferred embodiment of the method of the invention, said target cell population comprises at least 10%, 20%, 30%, 40% or at least 50% of the cells displaying at least one or more (or all) of the following characteristics of the aging phenotype:
- upregulation of the tumor suppressors $p16^{INK4a}$ and $p21^{CIP1}$ (hereafter referred as senescence effectors),
- cells arrested irreversibly in G1,
- expression of senescent-associated β-galactosidase activity (SA β-Gal),
- expression of senescence-associated heterochromatic foci (SAHF),
- altered overall mitochondrial activity.

In another specific embodiment, said target cell population are cells, such as dermal cells or fibroblast cells, obtained from an adult subject being at least 50 years old, for example at least 60, 70, 80, 90 or at least 100 years old.

Such target cell population may be obtained from mammal species, and preferably from rodent, primate or human species, more preferably from human species.

The target cell population may be obtained from various tissues, preferably from a human aged patient in need of autologous regenerative treatment.

Methods to obtain samples from various tissues and methods to establish primary cells are well-known in the art (see e.g. Jones and Wise, Methods Mol. Biol. 1997).

In one specific embodiment, said target cell population is obtained from primary cells from blood, bone marrow, adipose tissue, skin, hair, skin appendages, internal organs such as heart, gut or liver, mesenchymal tissues, muscle, bone, cartilage or skeletal tissues.

The Combination of Reprogramming Factors for Use in Rejuvenating or Generating iPSCs One essential feature of the present invention is the use of the following combination of reprogramming factors for use in rejuvenating or inducing pluripotent stem cells from the target cell population:
  i. a reprogramming factor encoded by one gene of the Oct family gene, preferably Oct4,
  ii. a reprogramming factor encoded by one gene of the Klf family gene, preferably Klf4,
  iii. a reprogramming factor encoded by one gene of the Sox family gene, preferably Sox2,
  iv. a reprogramming factor encoded by one gene of the Myc family gene, preferably c-Myc,
  v. Lin28, and, optionally,
  vi. Nanog.

The combination of reprogramming factors for use in rejuvenating or inducing pluripotent stem cells from the target cell population such as senescent cells or cells from aged donors, may include for example the combination of the 5 reprogramming factors Oct4, Klf4, Sox2, c-Myc (or L-myc) and Lin28, or the 6 reprogramming factors Oct4, Klf4, Sox2, c-Myc (or L-myc), Lin28 and Nanog. In one preferred embodiment, no functional inhibitors of p53 are used.

As used, herein, a functional inhibitor of p53 is any substance capable of inhibiting either (a) the function of the p53 protein or (b) the expression of the p53 gene. Such substances are for example described in WO 2011/016588. Most specifically, the present method does not contain the use of any means for expressing siRNA or shRNA against p53 into the target cell population (e.g the senescent cells).

As used herein, the term "Oct family" refers to the family of octamer ("Oct") transcription factors which play a crucial role in maintaining pluripotency. POU5F1 (POU domain, class 5, transcription factor 1) also known as Oct3/4 is one representative of Oct family. The absence of Oct3/4 in Oct-3/4+ cells, such as blastomeres and embryonic stem cells, leads to spontaneous trophoblast differentiation, and presence of Oct-3/4 thus gives rise to the pluripotency and differentiation potential of embryonic stem cells. Exemplary Oct3/4 proteins are the proteins encoded by the murine Oct3/4 gene (Genbank accession number NM_013633) and the human Oct3/4 gene (Genbank accession number NM_002701)

The terms "Oct3/4", "Oct4," "OCT4," "Oct4 protein," "OCT4 protein" and the like thus refer to any of the naturally-occurring forms of the Octomer 4 transcription factor, or variants thereof that maintain Oct4 transcription factor activity (e.g. within at least 50%, 80%, 90% or 100% activity compared to wild type Oct4 as measured by methods known in the art). In some embodiments, variants have at least 90% amino acid sequence identity across their whole sequence compared to the naturally occurring Oct4 polypeptide. In other embodiments, the Oct4 protein is the protein as identified by the Genbank reference ADW77327.1.

As used herein, the term "Sox family" refers to Sox genes associated with maintaining pluripotency similar to Oct-3/4, although it is associated with multipotent and unipotent stem cells in contrast with Oct-3/4, which is exclusively expressed in pluripotent stem cells. While Sox2 was the initial gene used for induction[1,3], other genes in the Sox family have been found to work as well in the induction process. Sox 1 yields iPSCs with a similar efficiency as Sox2, and genes Sox3, Sox15, and Sox18 also generate iPSCs.

Exemplary Sox2 proteins are the proteins encoded by the murine Sox2 gene (Genbank accession number NM_011443) and the human Sox2 gene (Genbank accession number NM_003106).

The terms "Sox2," "SOX2," "Sox2 protein," "SOX2 protein" and the like as referred to herein thus includes any of the naturally-occurring forms of the Sox2 transcription factor, or variants thereof that maintain Sox2 transcription factor activity (e.g. within at least 50%, 80%, 90% or 100% activity compared to wild type Sox2 as measured by methods known in the art). In some embodiments, variants have at least 90% amino acid sequence identity across their whole sequence compared to the naturally occurring Sox2 polypeptide. In other embodiments, the Sox2 protein is the protein as identified by the NCBI reference NP_003097.1.

As used herein, the term "Klf family" refers to Klf genes initially identified as a factor for the generation of mouse iPSCs and also demonstrated to be a factor for generation of human iPSCs. Exemplary Klf4 proteins are the proteins encoded by the murine klf4 gene (Genbank accession number NM_010637) and the human klf4 gene (Genbank accession number NM_004235).

The terms "KLF4," "KLF4 protein" and the like as referred to herein thus includes any of the naturally-occurring forms of the KLF4 transcription factor, or variants thereof that maintain KLF4 transcription factor activity (e.g. within at least 50%, 80%, 90% or 100% activity compared to wild type KLF4 as measured by methods known in the art). In some embodiments, variants have at least 90% amino acid sequence identity across their whole sequence compared to the naturally occurring KLF4 polypeptide. In other embodiments, the KLF4 protein is the protein as identified by the NCBI reference NP_004226.3.

As used herein, factors of the Myc family refers to factors encoded by myc proto-oncogenes implicated in cancer. c-Myc was shown to be a factor implicated in the generation of mouse iPSCs and of human iPSCs. Exemplary c-Myc proteins are the proteins encoded by the murine c-myc gene (Genbank accession number NM_010849) and the human c-myc gene (Genbank accession number NM_002467). N-Myc or L-myc was also used as possible reprogramming factor replacing c-Myc The terms "c-Myc," "C-MYC," "c-Myc protein", "C-MYC protein" and the like as referred to herein thus includes any of the naturally-occurring forms of the cMyc transcription factor, or variants thereof that maintain cMyc transcription factor activity (e.g. within at least 50%, 80%, 90% or 100% activity compared to wild type cMyc as measured by methods known in the art). In some embodiments, variants have at least 90% amino acid sequence identity across their whole sequence compared to the naturally occurring c-Myc polypeptide. In other embodiments, the c-Myc protein is the protein as identified by the NCBI reference NP_002458.2.

The term "Nanog" or "nanog" refers to a transcription factor critically involved with self-renewal of undifferentiated embryonic stem cells. In humans, this protein is encoded by the NANOG gene. Exemplary nanog is the protein encoded by murine gene (Genbank accession number XM_132755) and human Nanog gene (Genbank accession number NM_024865).

The term "Nanog" or "nanog" and the like as referred to herein thus includes any of the naturally-occurring forms of the Nanog transcription factor, or variants thereof that maintain Nanog transcription factor activity (e.g. within at least 50%, 80%, 90% or 100% activity compared to wild type Nanog as measured by methods known in the art). In some embodiments, variants have at least 90% amino acid sequence identity across their whole sequence compared to the naturally occurring Nanog polypeptide. In other embodiments, the Nanog protein is the protein as identified by the NCBI reference NP_079141.

The term "Lin28" or "Lin-28 homolog A" is a protein that is encoded by the LIN28 gene in humans. It is a marker of undifferentiated human embryonic stem cells and encodes a cytoplasmic mRNA-binding protein that binds to and enhances the translation of the IGF-2 (Insulin-like growth factor 2) mRNA. Lin28 has also been shown to bind to the let-7 pre-miRNA and block production of the mature let-7 microRNA in mouse embryonic stem cells. Yu et al. demonstrated that it is a factor in iPSCs generation, although it is not mandatory[3]. Exemplary Lin28 is the protein encoded by murine gene (Genbank accession number NM_145833) and human Lin28 gene (Genbank accession number NM_024674).

The term "Lin28" or "Lin28 homolog A" and the like as referred to herein thus includes any of the naturally-occurring forms of the Lin28 transcription factor, or variants thereof that maintain Lin28 transcription factor activity (e.g. within at least 50%, 80%, 90% or 100% activity compared to wild type Lin28 as measured by methods known in the art). In some embodiments, variants have at least 90% amino acid sequence identity across their whole sequence compared to the naturally occurring Lin28 polypeptide. In other embodiments, the Lin28 protein is the protein as identified by the NCBI reference NP_078950.

As used herein, the percent identity between the two amino-acid sequences is a function of the number of identical positions shared by the sequences (i.e., % identity=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described below.

The percent identity between two amino-acid sequences can be determined using the algorithm of E. Meyers and W. Miller (Comput. Appl. Biosci., 4:11-17, 1988) which has been incorporated into the ALIGN program (version 2.0), using a PAM120 weight residue table, a gap length penalty of 12 and a gap penalty of 4.

The skilled person may select other corresponding reprogramming factors originating from other mammals, such as mice, rats, cows, horses, sheep, pigs, goats, camels, antelopes, and dogs. Advantageously the skilled person may select the corresponding reprogramming factor from the same species as the target cells used as starting material in the method of the invention.

The skilled person may also select analogues of one or more of the above reprogramming factors. As used herein the term "analogue" refers to a compound that has a different structure but provides the same result as the reprogramming factor for use in generating iPSCs, and can thus replace said reprogramming factor in a method for generating induced pluripotent stem cells.

For example, analogues of such reprogramming factors have been described in Wenlin Li and Sheng Ding. Trends in Pharmacological Sciences Volume 31, Issue 1, January 2010, Pages 36-45 or Feng et al. Cell Stem Cell. 2009 Apr. 3; 4(4):301-12 (see in particular analogues disclosed in Tables 1 and 2 of Feng et al., 2009).

Conditions for Increasing the Expression of Reprogamming Factor

Any conditions available in the art for increasing expression of a reprogramming factor can be used in the methods of the invention, as long as such conditions result in the presence of reprogramming factor in an appropriate amount for reprogramming said target cells to induced pluripotent stem cells.

Various methods for increasing expression of reprogramming factors have been described in the art. For a review, see Hanna J H, Saha K, Jaenisch R. Cell. 2010 Nov. 12; 143(4):508-25; or, Sheng Ding. Trends in Pharmacological Sciences Volume 31, Issue 1, January 2010, Pages 36-45; and, Feng et al. Cell Stem Cell. 2009 Apr. 3; 4(4):301-12.

In preferred embodiments, the following alternative may be used for increasing expression of the reprogramming factors:

(i) enhancing endogenous expression of the gene encoding said reprogramming factor, (ii) allowing ectopic expression of said reprogramming factor by introducing an expression vector comprising a coding sequence of said reprogramming factor operably linked to control sequences into the target cell population, or (iii) delivering into the cells an appropriate amount of said reprogramming factor or its precursor RNA.

In another embodiment, one or more expression vectors are used which comprise the coding sequence of the combination of reprogramming factors, for example, Oct4 coding sequence, Sox2 coding sequence, Klf4 coding sequence, c-Myc coding sequence, Lin28 coding sequence, and, optionally, Nanog coding sequence and/or coding sequences having at least 60%, 70%, 80%, 90% or 95% identity to the corresponding native coding sequences of Oct4, Sox2, Klf4, c-Myc, Lin28 and, optionally, Nanog.

As used herein, the term "coding sequence" relates to a nucleotide sequence that upon transcription gives rise to the encoded product. The transcription of the coding sequence in accordance with the present invention can readily be effected in connection with a suitable promoter. Preferably, the coding sequence corresponds to the cDNA sequence of a gene that gives rise upon transcription to a reprogramming factor.

The percent identity between two nucleotide sequences may be determined using for example algorithms such as the BLASTN program for nucleic acid sequences using as defaults a word length (W) of 11, an expectation (E) of 10, M=5, N=4, and a comparison of both strands.

Expression vectors for ectopic expression of the reprogramming factors may be, for example, plasmid vector, cosmid vector, bacterial artificial chromosome (BAC) vector, transposon-based vector (such as PiggyBac) or viral vector.

In one specific embodiment, the expression vectors used for increasing expression of said reprogramming factors are viral vectors. Examples of such viral vectors includes vectors originated from retroviruses such as HIV (Human Immunodeficiency Virus), MLV (Murine Leukemia Virus), ASLV (Avian Sarcoma/Leukosis Virus), SNV (Spleen Necrosis Virus), RSV (Rous Sarcoma Virus), MMTV (Mouse Mammary Tumor Virus), etc, lentivirus, Adeno-associated viruses, and Herpes Simplex Virus, but are not limited to.

Methods for generating induced pluripotent stem cells based on expression vectors encoding reprogramming factors have been described in the Art, see for example WO2007/69666, EP2096169-A1 or WO2010/042490.

Typically, the coding sequence of any reprogramming factors as used in the method of the invention, for example, Oct4 coding sequence, Sox2 coding sequence, Klf4 coding sequence, c-Myc coding sequence, Nanog coding sequence and/or Lin28 coding sequence, may be operably linked to control sequences, for example a promoter, capable of effecting the expression of the coding sequence in the target cell population. Such expression vector may further include regulatory elements controlling its expression, such as a promoter, an initiation codon, a stop codon, a polyadenylation signal and an enhancer. The promoter may be constitutive, or inducible. The vector may be self-replicable or may be integrated into the DNA of the host cell.

Alternatively, the vector for ectopic expression is a viral vector and viral particles are produced and used to introduce the coding sequence of said reprogramming factors into said target cell population comprising aged or senescent cells. The term «viral particles» is intended to refer to the particles containing viral structural proteins and a sequence coding said reprogramming factors.

Viral particles may be prepared by transforming or transfecting a packaging cell with a viral vector carrying the nucleotide coding sequences of said combination of reprogramming factors. In the examples below, viral particles are prepared from lentivirus.

The target cell population may then be transfected using the expression vectors as described above.

The term "transfection" or "transfecting" refers to a process of introducing nucleic acid molecules into a cell. The nucleic acid molecules may be gene sequences encoding complete proteins or functional portions thereof. Any appropriate transfection method is useful in the methods described herein.

Incorporating the coding sequence and its control sequences directly into the genome of the target cells may cause activating or inactivating mutations of oncogenes or tumor suppressor genes, respectively. For certain applications, in particular medical applications, it may be required to avoid any genetic modifications of the target cells.

In a third embodiment, the reprogramming factors, for example, Oct4, Sox2, Flk4, c-Myc, Nanog and Lin28, or corresponding coding DNA or RNA, are introduced into the target cells without integration of exogenous genetic material in the host DNA, i.e. without introduction of the nucleotide sequence in the cell's genome.

An expression vector such as a plasmid vector can be delivered into said cells for ectopic expression of the reprogramming factor, in the form of naked DNA. Alternatively, RNAs coding for said reprogramming factors either chemically modified or not, can be introduced into the cells to reprogram them (see for example Warren L, et al, 2010, Cell Stem Cell. November 5; 7(5):618-30).

Other expression vectors have been described for example in WO 2009115295.

These nucleic acids can be delivered into the target cells with the aid, for example, of a liposome or a cationic polymer, for example, using conventional transfection protocols in mammalian cells.

In particular, appropriate transfection methods that do not use viral DNA or viral particles as a delivery system to introduce the nucleic acid molecules into the target cell may be used in the methods described herein. Exemplary transfection methods include without limitation calcium phosphate transfection, liposomal transfection, nucleofection, sonoporation, transfection through heat shock, magnetofection and electroporation. In some embodiments, the nucleic acid molecules are introduced into the target cells using electroporation following standard procedures well known in the art.

Alternatively, the reprogramming factor protein or fragments thereof showing similar properties to the intact proteins with respect to the reprogramming of target cells can be delivered into said target cells with the aid of chemical carriers such as cell-penetrating peptides including, without limitation, penetratin or TAT-derived peptides.

Methods to improve efficiency of the generation of iPSCs have also been described in the Art. In particular, in the method of the invention, introduction and/or addition of various generation efficiency improving agents may be performed. Examples of substance for improving generation efficiency of iPSCs include, without limitation, histone deacetylase inhibitors (such as for example valproic acid, trichostatin A, sodium lactate, MC1293 and M344), and nucleic acid expression inhibitors such as siRNAs and shRNA for HDAC, and G9a histone methyltransferase inhibitors, and nucleic acid expression system inhibitors such as siRNA and shRNA for G9a (see also Feng et al., 2009, supra).

In one specific embodiment, the methods according to the invention do not comprise any step of direct silencing of senescence effectors, and in particular direct silencing of p53 effectors.

By "direct silencing", it is meant to use a substance that will act directly on the expression of the gene of interest, for example, p53 gene, and not on a substance that will act on a factor upstream. One way to silence a gene is the use of siRNA or shRNA directly directed on the gene sequence to inhibit.

Compositions Comprising iPSCs Obtainable from the Methods of the Invention

The invention further relates to a cell-based composition comprising iPSCs obtainable from the method as described above (hereafter referred as "the iPSCs compositions"), and a pharmaceutically acceptable vehicle. Remarkably, iPSCs according to the present invention have no characteristics of the aging phenotype, though deriving from cells from aged donors or senescent cells.

These iPSCs compositions typically may comprise iPSCs obtained from a patient suffering from aged-related disorder such as disorders caused by defective helicase, including Werner Syndrome, Cockayne, Rothmund-Thomson, and Bloom syndromes, and xeroderma pigmentosa and trichothiodystrophy, or other disorders including without limitation, Hutchinson-Giford progeria or Wiedemann-Rautenstrauch syndrome.

Composition of Cells Obtained by Differentiation of iPSCs Obtainable from the Methods of the Invention and Uses Thereof The iPSCs obtained from the methods of the invention, in particular from cells of aged donors, may advantageously be cultured in vitro under differentiation conditions, to generate differentiated cells, such as muscle, cartilage, bone, dermal tissue, cardiac or vascular tissue, or other tissues of interest.

Thus, the invention relates to the methods for preparing compositions comprising differentiated cells, said method comprising the steps of
  (a) providing a composition comprising iPS cells obtained from the methods of the invention from target cells of aged donors; and, (b) culturing said composition comprising iPS cells, under appropriate conditions for their differentiation into the desired cell lineages.

The skilled person may use known protocols for differentiating stem cells, such as induced pluripotent stem cells, ES cells or mesenchymal stem cells into the desired cell lineages.

Another aspect of the invention relates to the use of said composition comprising said cell lineages derived from differentiation of iPSC, hereafter referred as the Differentiated Cells of the Invention.

The Differentiated Cells of the Invention have the particularity to have a rejuvenated phenotype, for example, with respect to the size of the telomeres, gene expression profile, metabolism, and the number of cell cycle prior to appearance of senescence phenotype, while being derived from cells of aged donors, for example donors more than 70 years old. The Differentiated Cells of the Invention may thus be used in a variety of application, in particular, in research or therapeutic field.

One major field of application is cell therapy or regenerative medicine. These iPSCs or Differentiated Cells composition may also be useful for generating cellular models of aged-related disorders as described above.

For example, primary cells, such as fibroblast cells obtained from a patient suffering from a genetic defect, may be cultured and genetically corrected according to methods known in the art, and subsequently reprogrammed and rejuvenated into iPSCs according to the methods of the present invention and differentiated into the suitable cell lineages for re-administration into the patient, for example the same patient as the cell donor (autologous treatment).

Similarly, regenerative medicine can be used to potentially cure any disease that results from malfunctioning, damaged or failing tissue by either regenerating the damaged tissues in vivo by direct in vivo implanting of a composition comprising iPSCs or their derivatives comprising appropriate progenitors or cell lineages or differentiated cells of the Invention. Preferably, such damaged tissues are tissue damaged from aged-related disorders or aged patients, being more than 50, 60, 70, 80, 90 or more than 100 years old.

In one aspect, the iPS cells or the Differentiated Cells of the Invention may be useful for autologous regenerative therapy of a patient suffering from aged related disorders or an aged patient in need of regenerative therapy due to specific disorders or treatments associated to such disorders, including without limitation, cancer disorders, inflammatory and autoimmune disorders, muscle and skeletal disorders, neurologic disorders, diabete and other metabolic disorders.

Therefore, in one aspect, the invention relates to the iPSCs compositions or Differentiated Cells of the Invention for use as a cell therapy product for implanting into mammal, for example a human patient, preferably, an aged patient being more than 50, 60, 70, 80, 90 or more than 100 years old, most preferably as an autologous graft (i.e the cells have the same genotype as the patient's cells)

In another specific embodiment, the iPSCs compositions or Differentiated Cells of the Invention are used for the treatment of joint or cartilage, muscle or bone damages.

In another specific embodiment, the iPSCs compositions or Differentiated Cells of the Invention may also be used advantageously for the production of dermal tissues, for example, skin tissues, for use in regenerative medicine (cell-based therapy) or in research.

In another specific embodiment, the iPSCs compositions or Differentiated Cells of the Invention may also be used advantageously for the production of, but not restricted to, dermal, muscle or skeletal cells from healthy or diseased patients for screening applications in the pharmaceutical industry. Such screening tests can be used to search for new drugs with clinical applications or for toxicology tests.

In another specific embodiment, the iPSCs compositions or Differentiated Cells of the Invention may also be used for regenerating cardiac or vascular tissue.

In another specific embodiment, the iPSCs compositions or Differentiated Cells of the Invention may also be used for regenerating brain tissue or neuronal tissue, for example in patient suffering from neurodegenerative disorders.

Methods for Rejuvenating Target Cells

In another aspect, the invention relates to a method for rejuvenating cells from aged donors or senescent cells.

In particular, the invention relates to an in vitro method for rejuvenating cells from aged donors or senescent cells, said method comprising reprogramming said target cells to induced pluripotent stem cell, by increasing expression in said target cells of at least the following reprogramming factors:

(i) a reprogramming factor encoded by one gene of the Oct family gene, for example Oct4,
(ii) a reprogramming factor encoded by one gene of the Klf family gene, for example Klf4,
(iii) a reprogramming factor encoded by one gene of the Sox family gene, for example Sox2,
(iv) a reprogramming factor encoded by one gene of the Myc family gene, for example, c-myc or L-myc, and,
(v) Lin28,
(vi) and, optionally, Nanog.

The term "rejuvenating" refers to the process of erasing epigenetic modifications participating in the cellular aging phenotype. The cellular aging phenotype can be characterized, inter alia by the following markers:

activation of the $p53/p21^{CIP1}$ and $pRb/p16^{INK4A}$ tumor suppressor pathways (hereafter referred as senescence effectors),
cells arrested irreversibly in G1,
shortening of telomere size,
expression of senescent-associated β-galactosidase activity (SA β-Gal),
Specific chromatin modification as senescence-associated heterochromatic foci (SAHF),
Specific secretome,
reduced/altered overall mitochondrial activity.

A process of rejuvenation is observed when one or all of these markers of aging phenotype is reduced or suppressed in an aged or senescent cell type due to the rejuvenating process.

In one preferred embodiment, the in vitro method for rejuvenating cells from aged donors or senescent cells comprise culturing said cells from aged donors or senescent cells under appropriate conditions for increasing expression of the following combination of reprogramming factors consisting of Oct4, Klf4, Sox2, c-Myc, Lin28 and, optionally, Nanog.

The combination of reprogramming factors may be used in vivo for rejuvenating tissue of a subject in need thereof. Thus the invention further relates to a composition for in vivo use in rejuvenating senescent or aged cells in a subject in need thereof, said composition comprising means for increasing expression of the following combination of reprogramming factors consisting of Oct4, Klf4, Sox2, c-Myc, Lin28 and, optionally, Nanog.

In some embodiments, said means for increasing expression of said reprogramming factors comprises an appropriate amount of Oct4 protein, Klf4 protein, Sox2 protein, c-Myc protein, Lin28 protein and, optionally, Nanog protein, each protein being associated to appropriate means for delivery of said protein into the nucleus of the senescent cells to be rejuvenated.

Means for delivery of a protein into a cell includes, without limitation, the chemical carriers such as cell-penetrating peptides such as penetratin or TAT-derived peptides.

In other embodiments, said means for increasing expression of said reprogramming factors comprise an appropriate amount of Oct4 precursor RNA, Klf4 precursor RNA, Sox2 precursor RNA, c-Myc precursor RNA, Lin28 precursor RNA and, optionally, Nanog precursor RNA, associated to appropriate means for delivery of each precursor RNA into the cytoplasm of the senescent cells to be rejuvenated.

These compositions as described above are particularly suitable for topical application, for example for skin or dermal application, for example for treating skin disorders.

The invention will be further illustrated by the following examples. However, these examples should not be interpreted in any way as limiting the scope of the present invention.

EXAMPLES

Methods

Cells from aged donors were obtained from the Coriell Institute for Medical Research (NJ, USA). Replicative senescent cells were obtained by extensive cell culture until cell cycle growth arrest, assessed by FACS, and senescence-Associated β-Galactosidase activity detected as previously described[25].

H9 and H1 human embryonic stem cells were obtained from the WiCell Research Institute (WI, USA). hESCs and iPSCs were either maintained using standard hESC procedures on Mitomycin-C treated OF-1 mouse embryonic fibroblasts (MEF) in KO DMEM culture medium (hESC medium) supplemented with 20% KnockOut serum replacement, 0.1 mM non-essential amino acids, 2 mM L-glutamine (all from Invitrogen), 0.1 mM β-mercaptoethanol and 10 ng/ml basic fibroblast growth factor (bFGF, Peprotech) or in feeder-free culture on matrigel (BD Biosciences) with chemically defined mTeSR medium (Stemcell Technologies) as previously described[26].

For generation of human iPSCs, lentiviral vectors containing cDNAs of human OCT4, SOX2, NANOG and LIN28 genes were obtained from Addgene and previously described by Yu et al[3]. KLF4 and c-MYC cDNAs were subcloned into the same vector backbone from vectors described by Takahashi et al.[2,3]. The 293T cell line (Invitrogen) was used to produce transgene-expressing lentiviruses. Human primary fibroblasts were seeded at $2 \cdot 10^5$ cells per 35 mm dish one day before transduction. Equal amounts of supernatants containing each of the six lentiviruses were mixed, transferred to the fibroblast dish, and incubated overnight. Twenty-four hours after transduction, the lentivirus-containing medium was replaced with the second supernatant. Six days after transduction, fibroblasts were harvested by trypsinization and replated in a 100 mm dish on MEF feeder layer. Next day, the medium was replaced with hESCs medium supplemented with 10 ng/ml bFGF. The medium was changed every other day. Thirty at forty days after transduction, colonies were picked up and transferred into 35 mm dish on a feeder layer with 2 ml of hESCs medium supplemented with 10 ng/ml bFGF.

Results 74-year-old donor proliferative human diploid fibroblasts (hereafter 74P) were induced into replicative senescence by serial passaging (74S). Cellular senescence was assessed after 18 passages (51 population doublings) by FACS analysis, increase in SA-β-Gal activity, up-regulation of the CDK inhibitors $p16^{INK4A}$ and $p21^{CIP1}$ and the formation of SAHFs. These senescent cells were also maintained more than 2 months in culture without any detectable increase in the cell number, confirming the robustness of cell cycle arrest. We initially tried to generate iPSCs from these senescent fibroblasts by overexpression of the LIN28-containing set of genes (OCT4, NANOG, SOX2, LIN28) to compare with previous experimental results published with the set of 4 reprogramming factors OCT4, SOX2, KLF4, c-MYC and originally described as inefficient for senescence bypass. All of these reprogramming factor genes were transduced by individual lentiviruses. After 40 days, we did not observe any new proliferation or formation of hESC colonies resembling iPSCs. This was confirmed by the absence of detectable expression of endogenous pluripotency genes in the infected cell population, whereas quantitative RT-PCR demonstrated efficient viral transduction. These results demonstrate that the LIN28-containing set of reprogramming factors is not able to reverse the replicative senescence state to generate iPSCs, as previously described with the OCT4, SOX2, KLF4, c-MYC combination.

Interestingly, NANOG overexpression has been described to accelerate reprogramming in a predominantly cell-division-rate-independent manner, and overexpression of LIN28, similar to inhibition of the $p53/p21^{CIP1}$ pathway, increases the cell division rate, resulting in an accelerated kinetics of iPSCs production[13,14]. We therefore hypothesized that the senescence barrier might be overcome using a protocol optimized for an increased reprogramming efficiency based on the combination of the 6 reprogramming factors OCT4, NANOG, SOX2, KLF4, LIN28, and c-MYC introduced by individual lentiviral particles, without additional transient or permanent inhibition of senescence inductors.

To test our hypothesis, 74P and 74S cells were infected twice with a mix of the individual lentiviruses carrying each of the 6 genes. One week after infection, we observed disappearance of SAHFs in infected senescent fibroblasts (74S inf) revealing a first step of reprogramming. Then, cells were plated onto mouse fibroblast feeders in hESCs medium, and after 18-20 days, proliferation was recovered in infected senescent cells. Colonies resembling hESCs appeared at 35-40 days post-infection. iPSC-like colonies were produced from senescent fibroblasts (74S), with a mean reprogramming efficiency of 0.015-0.03%, similar to proliferative fibroblasts (74P), infected under the same conditions. We randomly selected 6 colonies from proliferative (iPSC 74P) and senescent (iPSC 74S) 74-year-old donor fibroblasts, and further characterized 3 clones, which were then successfully expanded in either regular hESCs feeder or feeder-free culture conditions. Long-term culture and assessment for the expression of stem cell markers confirmed successful maintenance and reprogramming of these cells, which have now been grown for more than 35 passages. Immunocytochemistry analysis demonstrated the continued presence of the cell surface markers SSEA-4 and TRA-1-60 that characterize human pluripotent stem cells. Quantitative RT-PCR analyses showed that the iPSCs re-expressed endogenous OCT4, SOX2, NANOG and the REX1 pluripotent marker genes at the same level as H1 and H9 hESC lines or the IMR90 clone 4 iPSC line generated in the Thomson Laboratory (iPSC IMR90TH Cl 4[3]) and grown in parallel, while no transcript was detected in the parental fibroblasts. In order to corroborate this reactivation of endogenous genes, we investigated the DNA methylation status of CpG dinucleotides in one described CpG-rich region in OCT4 and NANOG promoters. Bisulfite genomic sequencing analysis showed that both the OCT4 and NANOG promoters were demethylated either in iPSCs from senescent (iPSC 74S Cl F) or proliferative (iPSC 74P Cl H) cells, as efficiently as the previously published iPSC IMR90TH Cl 4[3], when compared to the methylation status of hESC H9, whereas the same regions were highly methylated in parental fibroblasts.

To exclude any cell type-specific effects, we repeated the same protocol using the IMR90 human embryonic fibroblasts induced into replicative senescence by serial passaging. Similar to the 74-year-old donor fibroblasts, we did not succeed in generating iPSCs using both sets of 4 factors described previously, whereas we obtained similar reprogramming efficiency from proliferative or senescent IMR90 fibroblasts with the combination of the 6 factors.

Next we assessed the pluripotent state of our generated iPSCs by evaluating the differentiation abilities of iPSC 74S compared to the iPSC 74P clones. All iPSCs were able to differentiate into the three early embryonic lineages, endoderm, ectoderm and mesoderm, as demonstrated using immunostaining with specific antibodies against SMA, MAP2 and FOXA2 respectively. We obtained similar results with senescent IMR90 fibroblasts. Altogether, these results indicate that the combination of the 6 transcription factors, OCT4, NANOG, SOX2, KLF4, LIN28, and c-MYC is a successful reprogramming strategy for reversing the cellular senescence state leading to generation of iPSCs.

During aging, the number of senescent cells increases in the human body, and is thought to impair tissue homeostasis. However, increased expression of $p16^{INK4A}$ and $p21^{CIP1}$ occurs in proliferative cells from aged donors, and is thought to decrease progressively their proliferative capacity[15]. Whether proliferative cells from centenarians might be efficiently reprogrammed towards pluripotency, and whether they retain some specific markers of the cellular aging phenotype, is an unresolved issue. To investigate this specific point, we used fibroblasts from 92-, 94-, 96- and 101-year-old donors for reprogramming experiments, by using the 6 factors in combination. As suggested by our previous experiments on senescent cells, we were able to generate iPSCs from all the aged donor fibroblasts, with similar efficiency to those obtained with senescent fibroblasts. All iPSC clones generated re-expressed endogenous pluripotency genes OCT4, SOX2, NANOG and REX1, as presented for two clones for each parental fibroblast line, that was also confirmed by demethylation of CpG in the OCT4 and NANOG promoter regions. Interestingly, we also observed partial demethylation of the NANOG promoter in parental fibroblasts from aged donors that is in accordance with the global demethylation of the genome already described in the elderly[16], that might also have contributing effects in reprogramming. In addition, we detected re-expression of the pluripotency cell surface markers SSEA-4 and TRA-1-60, and finally, we demonstrated their ability to differentiate into endoderm, ectoderm and mesoderm derivatives as judged by immunostaining with SMA, MAP2 and FOXA2 antibodies respectively.

These results demonstrate the efficiency of our reprogramming procedure to successfully reinstate the pluripotent state and self-renewal from centenarian fibroblasts; thus, cellular aging and the frequently-associated senescent phenotype is not a limit to reprogramming towards pluripotency.

Although we succeeded in generating iPSCs using aged donors and senescent fibroblasts, an essential issue was to elucidate whether induction of a pluripotent state might erase the main markers of the cellular aging phenotype. We previously showed that reprogramming induced SAHF disappearance, demonstrating the genome organization plasticity of senescent cells. We then analyzed other hallmarks of aging and senescence in our iPSCs and found that iPSCs generated from replicative senescent fibroblasts from the 74-year-old donor did not retain increased expression of $p21^{CIP1}$ and $p16^{INK4A}$ inherited from their previous senescent state, as shown by immunoblot analysis. Similar results were also obtained with IMR90 embryonic replicative senescent fibroblasts. In addition, all iPSCs generated from centenarians also have downregulated expression of $p21^{CIP1}$ and $p16^{INK4A}$ proteins, similar to hESC lines. These results indicate that we were able to reset the expression of $p21^{CIP1}$ and $p16^{INK4A}$ to the low level found in hESCs.

Proliferative fibroblasts from aged donors are usually characterized by telomeres of heterogeneous size, whose mean length depends on the parental inherited size and on the various number of divisions occurring during the lifespan, but which do not necessarily correlate with proliferation capacity. However replicative senescence is always associated with short telomeres. Short telomeres are recognized as damaged DNA, leading to activation of the DNA damage response signaling cascade and triggering senescence-associated cell cycle arrest. Although, iPSCs generally exhibit an increased telomere size compared to the parental differentiated cells[17], we wondered whether iPSCs obtained from senescent cells or from centenarian cells exhibited telomeres of increased length. To address this question, we used Southern blot analysis to examine the mean terminal restriction fragment (TRF) length of iPSCs obtained from replicative senescent cells, compared to proliferative cells. We found that telomere length of iPSCs from the aged 74 donor, both from proliferative or senescent cells, increased to a size equivalent to those observed in H9 hESC. Unlike parental fibroblasts, which entered into replicative senescence after 50 population doublings, and 60-63 doublings for embryonic fibroblasts IMR90, we were able, to culture all iPSC lines continuously, which remained stable after more than 110 population doublings. Similarly, telomeric DNA length was increased in iPSCs derived from senescent or proliferative IMR90 embryonic fibroblasts, after reprogramming. Although, telomeres from centenarians were shortened less in size than in senescent fibroblasts, we were able to reset their size to the same length as hESCs. Interestingly, in some iPSC clones, we found a longer upper size than found in H9 hESC, suggesting that telomere size in pluripotent cells does not have an inherited maximum size. It also suggests some possible additional developments in iPSC generation for increased proliferation ability of differentiated cells, suitable for cell-based therapy in regenerative medicine.

Collectively, these data highlight that our reprogramming protocol leads to erasure of the most common marks of senescence and aging in the generated iPSCs.

To further evaluate the pluripotent capacity of senescent and aged derived iPSCs, we selected 3 iPSC clones from aged proliferative and senescent fibroblasts, iPSC 74P Cl H, iPSC 74S Cl F and iPSC 96 Cl 1. We first confirmed the full capacity of these clones to progress into terminal differentiation by the formation of teratoma in mice, leading to appearance of organized organ-like structures in the three embryonic lineages. DNA fingerprinting analyses (short tandem repeat, STR) were also performed to confirm that iPSC clones were derived from their corresponding parental fibroblasts. We also verified that the 6 transgenes used for the reprogramming were almost completely down-regulated.

Then, we performed transcriptome analysis of 3 selected clones and their parental counterpart, that we compared to a hESCs and iPSCs data set, built as a compendium ([18]). We first confirmed that the specific pluripotent genes were expressed in our iPSCs at a similar level as hESCs and iPSCs from the compendium ([19]). Then, we performed a hierarchical clustering of our 3 iPSC clones and their parental fibroblasts, combined with several hESCs, iPSCs and post-natal fibroblasts. Strikingly, we found that, proliferative, senescent and aged fibroblasts were clustered together compared to post-natal fibroblasts, suggesting that they share a general common aging signature. Further, the derived iPSCs from proliferative and senescent aged fibroblasts obtained using the infection of the 6 factors are significantly more similar to hESCs than previously described iPSCs derived from a 4 factor infection.

Since oxidative stress and mitochondrial dysfunction are well described in senescence and aging[20,21], we wondered whether these functions were also specifically reprogrammed from senescent and aged cells. Transcriptome analysis allowed us to study genes involved in both processes, as previously described[22]. Again, clustering of transcriptomes with this subset of specific genes indicated that global modifications in expression profiles associated with these altered functions were specific to aged and senescent fibroblasts, when compared to young proliferative embryonic or post-natal fibroblasts, and that our derived iPSCs have reset these functions to an embryonic-like status. Next, we evaluated the overall mitochondrial activity in the derived iPSCs compared to hESCs, by measuring the ($\Delta\Psi$m) transmembrane potential generated by the proton gradient, which is an indicator of healthy mitochondrial function. For this purpose, we used the cationic dye JC-1 and quantified the fluorescence intensity ratio of its two forms by confocal microscopy and flow cytometry analysis. As previously shown, the red/green ratio decreased with senescence[20,21] and also seems associated with aging. Strikingly, we found an increased ratio in iPSCs to a level similar to that found in hESCs, confirming that reprogramming restored the mitochondrial activity of iPSCs derived from old and senescent fibroblasts. Similar results were obtained with iPSCs from proliferative or senescent IMR90 fibroblasts. Furthermore, we did not observe differences in distribution and morphology of mitochondria in iPSCs by electronic microscopy when compared to H1 hESC. Analysis of mitochondrial properties illustrates how nuclear reprogramming, in resetting gene expression programs, might rejuvenate to a healthy cell physiology through restoring impaired function of cellular organelles whose dysfunction is involved in cellular aging. Finally, using a fibroblasts differentiation assay[23,24], we demonstrated that these cells did not enter prematurely into senescence. Indeed, fibroblasts derived from 74P, S and 96 iPSCs did not reveal SA-$\beta$-Gal activity after 10 population doublings, and exhibited a proliferation rate equivalent to young proliferative fibroblasts. To exclude the possibility that our reprogramming strategy was not associated with any mutations in the senescence induction pathways, we demonstrated the ability of re-differentiated fibroblasts to re-enter into replicative senescence. After extensive culture, these cells became senescent, as shown by increased SA-$\beta$-Gal activity associated with cell cycle arrest, the re-increased expression of $p16^{INK4A}$, and $p21^{CIP1}$ and a re-shortened telomere size. More interestingly, the number of population doublings (PD) necessary to trigger replicative senescence was increased. While the age 74 parental fibroblasts entered into replicative senescence after 51 PD, the re-differentiated fibroblasts from iPSC 74S Cl F entered into replicative senescence only after 58 PD. This re-acquired proliferation potential is similar to iPSC 74P Cl H derived from the age 74 proliferative parental fibroblasts PD 60, which was infected at PD 12. These cells exhibited a population doubling potential of 39 PD before exhaustion by replicative senescence. A similar resetting of the proliferation ability of the age 96 fibroblasts was observed and explained by the lengthening of telomeres. We conclude that our reprogramming strategy, which overcame the senescent state, was also able to increase the cellular lifespan. Transcriptome analysis by hierarchical clustering, comparing parental fibroblasts with post-natal and differentiated H1 hESCs in fibroblasts, finally demonstrated that the global gene expression profile of early re-differentiated fibroblasts from our iPSCs generated from old donors and senescent fibroblasts are distinct from parental fibroblasts, and closer to embryonic fibroblasts derived from the H1 hESC line. This result was also confirmed by gene expression profiles associated with oxidative stress and mitochondrial activity, confirming the rejuvenated physiology of our aged and senescent cells.

Taken together, our results show that it is possible to reprogram replicative senescent cells and cells derived from centenarians into iPSCs using a specific combination of genes, demonstrating that aging and senescence are not a barrier to reprogramming towards pluripotency. It also improves our understanding of fundamental cell reprogramming and underlines the underestimated importance of epigenetic modifications participating in the cellular aging process, which is evidently susceptible to be reprogrammed as well. But most importantly, we also demonstrate that, using an adequate reprogramming strategy, it is possible to rejuvenate the cell physiology, suggesting the potential reversibility of major aspects of the aging phenotype. These results also promote the potential development of age-related disease models, and support the development of new therapeutic cell-based strategies to erase some pathologies related to aging.

Useful Nucleotide and Amino Acid Sequences for Practicing the Methods of the Invention

TABLE 1

| NO: | Description | Sequence |
|---|---|---|
| 1 | Human Oct3/4 gene sequence (NM_002701) | CCTTCGCAAGCCCTCATTTCACCAGGCCCCCGGCTTGGGGCGCCTT CCTTCCCCATGGCGGGACACCTGGCTTCGGATTTCGCCTTCTCGCC CCCTCCAGGTGGTGGAGGTGATGGGCCAGGGGGGCCGGAGCCGGGC TGGGTTGATCCTCGGACCTGGCTAAGCTTCCAAGGCCCTCCTGGAG GGCCAGGAATCGGGCCGGGGGTTGGGCCAGGCTCTGAGGTGTGGGG GATTCCCCCATGCCCCCGCCGTATGAGTTCTGTGGGGGGATGGCG TACTGTGGGCCCCAGGTTGGAGTGGGGCTAGTGCCCCAAGGCGGCT TGGAGACCTCTCAGCCTGAGGGCGAAGCAGGAGTCGGGGTGGAGAG |

TABLE 1-continued

| NO: Description | Sequence |
|---|---|
| | CAACTCCGATGGGGCCTCCCCGGAGCCCTGCACCGTCACCCCTGGT<br>GCCGTGAAGCTGGAGAAGGAGAAGCTGGAGCAAAACCCGGAGGAGT<br>CCCAGGACATCAAAGCTCTGCAGAAAGAACTCGAGCAATTTGCCAA<br>GCTCCTGAAGCAGAAGAGGATCACCCTGGGATATACACAGGCCGAT<br>GTGGGGCTCACCCTGGGGGTTCTATTTGGGAAGGTATTCAGCCAAA<br>CGACCATCTGCCGCTTTGAGGCTCTGCAGCTTAGCTTCAAGAACAT<br>GTGTAAGCTGCGGCCCTTGCTGCAGAAGTGGGTGGAGGAAGCTGAC<br>AACAATGAAAATCTTCAGGAGATATGCAAAGCAGAAACCCTCGTGC<br>AGGCCCGAAAGAGAAAGCGAACCAGTATCGAGAACCGAGTGAGAGG<br>CAACCTGGAGAATTTGTTCCTGCAGTGCCCGAAACCCACACTGCAG<br>CAGATCAGCCACATCGCCCAGCAGCTTGGGCTCGAGAAGGATGTGG<br>TCCGAGTGTGGTTCTGTAACCGGCGCCAGAAGGGCAAGCGATCAAG<br>CAGCGACTATGCACAACGAGAGGATTTTGAGGCTGCTGGGTCTCCT<br>TTCTCAGGGGGACCAGTGTCCTTTCCTCTGGCCCCAGGGCCCCATT<br>TGGTACCCCAGGCTATGGGAGCCCTCACTTCACTGCACTGTACTC<br>CTCGGTCCCTTTCCCTGAGGGGGAAGCCTTTCCCCCTGTCTCCGTC<br>ACCACTCTGGGCTCTCCCATGCATTCAAACTGAGGTGCCTGCCCTT<br>CTAGGAATGGGGGACAGGGGGAGGGGAGGAGCTAGGGAAAGAAAAC<br>CTGGAGTTTGTGCCAGGGTTTTTGGGATTAAGTTCTTCATTCACTA<br>AGGAAGGAATTGGGAACACAAAGGGTGGGGGCAGGGGAGTTTGGGG<br>CAACTGGTTGGAGGGAAGGTGAAGTTCAATGATGCTCTTGAT<br>TTTAATCCCACATCATGTATCACTTTTTTCTTAAATAAAGAAGCCT<br>GGGACACAGTAGATAGACACACTTAAAAAAAAAAA |
| 2 Human Oct4 amino<br>acid sequence<br>(ADW77327.1) | MAGHLASDFAFSPPPGGGDGPGGPEPGWVDPRTWLSFQGPPGGPG<br>IGPGVGPGSEVWGIPPCPPPYEFCGGMAYCGPQVGVGLVPQGGLET<br>SQPEGEAGVGVESNSDGASPEPCTVTPGAVKLEKEKLEQNPEESQD<br>IKALQKELEQFAKLLKQKRITLGYTQADVGLTLGVLFGKVFSQTTI<br>CRFEALQLSFKNMCKLRPLLQKWVEEADNNENLQEICKAETLVQAR<br>KRKRTSIENRVRGNLENLFLQCPKPTLQQISHIAQQLGLEKDVVRV<br>WFCNRRQKGKRSSSDYAQREDFEAAGSPFSGGPVSFPLAPGPHFGT<br>PGYGSPHFTALYSSVPFPEGEAFPPVSVTTLGSPMHSN |
| 3 Human Sox2 gene<br>sequence<br>(NM_003106) | CTATTAACTTGTTCAAAAAGTATCAGGAGTTGTCAAGGCAGAGAA<br>GAGAGTGTTTGCAAAAAGGGAAAAGTACTTTGCTGCCTCTTTAAGA<br>CTAGGGCTGGGAGAAAGAAGAGGAGAGAAAGAAAGGAGAGAAGT<br>TTGGAGCCCGAGGCTTAAGCCTTTCCAAAAACTAATCACAACAATC<br>GCGGCGGCCCGAGGAGGAGAGCGCCTGTTTTTTCATCCCAATTGCA<br>CTTCGCCCGTCTCGAGCTCCGCTTCCCCCCAACTATTCTCCGCCAG<br>ATCTCCGCGCAGGGCCGTGCACGCCGAGGCCCCGCCCGCGGCCCC<br>TGCATCCCGGCCCCCGAGCGCGGCCCCCACAGTCCCGGCCGGGCCG<br>AGGGTTGGCGGCCGCCGGCGGGCCGCGCCCGCCCAGCGCCCGCATG<br>TATAACATGATGGAGACGGAGCTGAAGCCGCCGGGCCCGCAGCAAG<br>CTTCGGGGGGCGGCGGCGGAGGAGGCAACGCCACGGCGGCGGCGAC<br>CGGCGGCAACCAGAAGAACAGCCCGGACCGCGTCAAGAGGCCCATG<br>AACGCCTTCATGGTATGGTCCCGGGGGCAGCGGCGTAAGATGGCCC<br>AGGAGAACCCCAAGATGCACAACTCGGAGATCAGCAAGCGCCTGGG<br>CGCGGAGTGGAAACTTTTGTCCGAGACCGAGAAGCGGCCGTTCATC<br>GACGAGGCCAAGCGGCTGCGCGCTCTGCACATGAAGGAGCACCCGG<br>ATTATAAATACCGGCCGCGGCGGAAAACCAAGACGCTCATGAAGAA<br>GGATAAGTACACGCTTCCCGGAGGCTTGCTGGCCCCGGCGGGAAC<br>AGCATGGCGAGCGGGGTTGGGGTGGGCGCCGGCCTGGGTGCGGGCG<br>TGAACCAGCGCATGGACAGCTACGCGCACATGAACGGCTGGAGCAA<br>CGGCAGCTACAGCATGATGCAGGAGCAGCTGGGCTACCCGCAGCAC<br>CCGGGCCTCAACGCTCACGGCGCGGCACAGATGCAACCGATGCACC<br>GCTACGACGTCAGCGCCCTGCAGTACAACTCCATGACCAGCTCGCA<br>GACCTACATGAACGGCTCGCCCACCTACAGCATGTCCTACTCGCAG<br>CAGGGCACCCCCGGTATGGCGCTGGGCTCCATGGGCTCTGTGGTCA<br>AGTCCGAGGCCAGCTCCAGCCCCCCGTGGTTACCTCTTCCTCCCA<br>CTCCAGGGCGCCCTGCCAGGCCGGGGACCTCCGGGACATGATCAGC<br>ATGTACCTCCCCGGCGCCGAGGTGCCGGAGCCCGCTGCGCCCAGTA<br>GACTGCACATGGCCCAGCACTACCAGAGCGGCCCGGTGCCCGGCAC<br>GGCCATTAACGGCACACTGCCCCTGTCGCACATGTGAGGGCTGGAC<br>TGCGAACTGGAGAAGGGGAGAGATTTTCAAAGAGATACAAGGGAAT<br>TGGGAGGGGTGCAAAAAGAGGAGAGTAGGAAAAATCTGATAATGCT<br>CAAAAGGAAAAAAAATCTCCGCAGCGAAACGACAGCTGCGGAAAAA<br>AACCACCAATCCCATCCAAATTAACGCAAAAACCGTGATGCCGACT<br>AGAAAACTTTTATGAGAGATCTTGGGACTTCTTTTGGGGGACTAT<br>TTTTGTACAGAGAAAACCTGAGGGCGGCGGGGAGGGCGGGGGAATC<br>GGACCATGTATAGATCTGGAGGAAAAAAACTACGCAAAACTTTTTT<br>TTAAAGTTCTAGTGGTACGTTAGGCGCTTCGCAGGGAGTTCGCAAA<br>AGTCTTTACCAGTAATATTTAGAGCTAGACTCCGGGCGATGAAAAA<br>AAAGTTTTAATATTTGCAAGCAACTTTTGTACAGTATTTATCGAGA<br>TAAACATGGCAATCAAATGTCCATTGTTTATAAGCTGAGAATTTGC<br>CAATATTTTCGAGGAAAGGGTTCTTGCTGGGTTTTGATTCTGCAG<br>CTTAAATTTAGGACCGTTACAAACAAGGAAGGAGTTTATTCGGATT<br>TGAACATTTTAGTTTTAAAATTGTACAAAAGGAAAACATGAGAGCA<br>AGTACTGGCAAGACCGTTTTCGTGGTCTTGTTTAAGGCAAACGTTC |

TABLE 1-continued

| NO: | Description | Sequence |
|---|---|---|
| | | TAGATTGTACTAAATTTTTAACTTACTGTTAAAGGCAAAAAAAAA<br>TGTCCATGCAGGTTGATATCGTTGGTAATTTATAATAGCTTTTGTT<br>CAATCCTACCCTTTCATTTTGTTCACATAAAAAATATGGAATTACT<br>GTGTTTGAAATATTTTCTTATGGTTTGTAATATTTCTGTAAATTGT<br>GATATTTTAAGGTTTTTCCCCCCTTTTATTTTCCGTAGTTGTATTT<br>TAAAAGATTCGGCTCTGTTATTGGAATCAGGCTGCCGAGAATCCAT<br>GTATATATTTGAACTAATACCATCCTTATAACAGCTACATTTTCAA<br>CTTAAGTTTTTACTCCATTATGCACAGTTTGAGATAAATAAATTTT<br>TGAAATATGGACACTGAAA |
| 4 | Human Sox2 amino acid sequence (NCBI ref NP_003097.1) | MYNMMETELKPPGPQQTSGGGGGNSTAAAAGGNQKNSPDRVKRPMN<br>AFMVWSRGQRRKMAQENPKMHNSEISKRLGAEWKLLSETEKRPFID<br>EAKRLRALHMKEHPDYKYRPRRKTKTLMKKDKYTLPGGLLAPGGNS<br>MASGVGVGAGLGAGVNQRMDSYAHMNGWSNGSYSMMQDQLGYPQHP<br>GLNAHGAAQMQPMHRYDVSALQYNSMTSSQTYMNGSPTYSMSYSQQ<br>GTPGMALGSMGSVVKSEASSSPPVVTSSSHSRAPCQAGDLRDMISM<br>YLPGAEVPEPAAPSRLHMSQHYQSGPVPGTAINGTLPLSHM |
| 5 | Human Klf4 gene sequence (NM_004235) | AGTTTCCCGACCAGAGAGAACGAACGTGTCTGCGGGCGCGCGGGGA<br>GCAGAGGCGGTGGCGGGCGGCGGCGGCACCGGGAGCCGCCGAGTGA<br>CCCTCCCCCGCCCCTCTGGCCCCCCACCCTCCCACCCGCCCGTGGC<br>CCGCGCCCATGGCCGCGCGCGCTCCACACAACTCACCGGAGTCCGC<br>GCCTTGCGCCGCCGACCAGTTCGCAGCTCCGCGCCACGGCAGCCAG<br>TCTCACCTGGCGGCACCGCCCGCCCACCGCCCCGGCCACAGCCCCT<br>GCGCCCACGGCAGCACTCGAGGCGACCGCGACAGTGGTGGGGACG<br>CTGCTGAGTGGAAGAGAGCGCAGCCCGGCCACCGGACCTACTTACT<br>CGCCTTGCTGATTGTCTATTTTTGCGTTTACAACTTTTCTAAGAAC<br>TTTTGTATACAAAGGAACTTTTTAAAAAAGACGTTCCAAGTTATA<br>TTTAATCCAAAGAAGAAGGATCTCGGCCAATTTGGGGTTTTGGGTT<br>TTGGCTTCGTTTCTTCTCTTCGTTGACTTTGGGGTTCAGGTGCCCC<br>AGCTGCTTCGGGCTGCCGAGGACCTTCTGGGCCCCACATTAATGA<br>GGCAGCCACCTGGCGAGTCTGACATGGCTGTCAGCGACGCGCTGCT<br>CCCATCTTTCTCCACGTTCGCGTCTGGCCCGGCGGGAAGGGAGAAG<br>ACACTGCGTCAAGCAGGTGCCCCGAATAACCGCTGGCGGGAGGAGC<br>TCTCCCACATGAAGCGACTTCCCCCAGTGCTTCCCGGCCGCCCCTA<br>TGACCTGGCGGCGGCGACCGTGGCCACAGACCTGGAGAGCGGCGGA<br>GCCGGTGCGGCTTGCGGCGGTAGCAACCTGGCGCCCCTACCTCGGA<br>GAGAGACCGAGGAGTTCAACGATCTCCTGGACCTGG<br>ACTTTATTCTCTCCAATTCGCTGACCCATCCTCCGGAGTCAGTGGC<br>CGCCACCGTGTCCTCGTCAGCGTCAGCCTCCTCTTCGTCGTCGCCG<br>TCGAGCAGCGGCCCTGCCAGCGCGCCCTCCACCTGCAGCTTCACCT<br>ATCCGATCCGGGCCGGGAACGACCCGGGCGTGGCGCCGGGCGGCAC<br>GGGCGGAGGCCTCCTCTATGGCAGGGAGTCCGCTCCCCCTCCGACG<br>GCTCCCTTCAACCTGGCGGACATCAACGACGTGAGCCCCTCGGGCG<br>GCTTCGTGGCCGAGCTCCTGCGGCCAGAATTGGACCCGGTGTACAT<br>TCCGCCGCAGCAGCCGCAGCCGCCAGGTGGCGGGCTGATGGGCAAG<br>TTCGTGCTGAAGGCGTCGCTGAGCGCCCCTGGCAGCGAGTACGGCA<br>GCCCGTCGGTCATCAGCGTCAGCAAAGGCAGCCCTGACGGCAGCCA<br>CCCGGTGGTGGTGGCGCCCTACAACGGCGGGCCGCCGCGCACGTGC<br>CCCAAGATCAAGCAGGAGGCGGTCTCTTCGTGCACCCACTTGGGCG<br>CTGGACCCCCTCTCAGCAATGGCCACCGGCCGGCTGCACACGACTT<br>CCCCCTGGGGCGGCAGCTCCCCAGCAGGACTACCCCGACCCTGGGT<br>CTTGAGGAAGTGCTGAGCAGCAGGGACTGTCACCCTGCCCTGCCGC<br>TTCCTCCCGGCTTCCATCCCCACCCGGGGCCCAATTACCCCATCCTT<br>CCTGCCCGATCAGATGCAGCCGCAAGTCCCGCCGCTCCATTACCAA<br>GAGCTCATGCCACCCGGTTCCTGCATGCCAGAGGGAGCCCAAGCCAA<br>AGAGGGGAAGACGATCGTGGCCCCGGAAAAGGACCGCCACCCACAC<br>TTGTGATTACGCGGGCTGCGGCAAAACCTACACAAAGAGTTCCCAT<br>CTCAAGGCACACCTGCGAACCCACACAGGTGAGAAACCTTACCACT<br>GTGACTGGGACGGCTGTGGATGGAAATTCGCCCGCTCAGATGAACT<br>GACCAGGCACTACCGTAAACACACGGGGCACCGCCCGTTCCAGTGC<br>CAAAAATGCGACCGAGCATTTTCCAGGTCGGACCACCTCGCCTTAC<br>ACATGAAGAGGCATTTTTAAATCCCAGACAGTGGATATGACCCACA<br>CTGCCAGAAGAGAATTCAGTATTTTTTACTTTTCACACTGTCTTCC<br>CGATGAGGGAAGGAGCCCAGCCAGAAAGCACTACAATCATGGTCAA<br>GTTCCCAACTGAGTCATCTTGTGAGTGGATAATCAGGAAAATGAG<br>GAATCCAAAAGACAAAAATCAAAGAACAGATGGGGTCTGTGACTGG<br>ATCTTCTATCATTCCAATTCTAAATCCGACTTGAATATTCCTGGAC<br>TTACAAAATGCCAAGGGGTGACTGGAAGTTGTGGATATCAGGGTA<br>TAAATTATATCCGTGAGTTGGGGGAGGGAAGACCAGAATTCCCT<br>TGAATTGTGTATTGATGCAATATAAGCATAAAAGATCACCTTGTAT<br>TCTCTTTACCTTCTAAAAGCCATTATTATGATGTTAGAAGAAGAGG<br>AAGAAATTCAGGTACAGAAAACATGTTTAAATAGCCTAAATGATGG<br>TGCTTGGTGAGTCTTGGTTCTAAAGGTACCAAACAAGGAAGCCAAA<br>GTTTTCAAACTGCTGCATACTTTGACAAGGAAAATCTATATTTGTC<br>TTCCGATCAACATTTATGACCTAAGTCAGGTAATATACCTGGTTTA<br>CTTCTTTAGCATTTTTATGCAGACAGTCTGTTATGCACTGTGGTTT<br>CAGATGTGCAATAATTTGTACAATGGTTTATTCCCAAGTATGCCTT |

TABLE 1-continued

| NO: | Description | Sequence |
|---|---|---|
| | | AAGCAGAACAAATGTGTTTTTCTATATAGTTCCTTGCCTTAATAAA<br>TATGTAATATAAATTTAAGCAAACGTCTATTTTGTATATTTGTAAA<br>CTACAAAGTAAAATGAACATTTTGTGGAGTTTGTATTTTGCATACT<br>CAAGGTGAGAATTAAGTTTTAAATAAACCTATAATATTTTATCTGA<br>AAAAAAAAAAAAAAAA |
| 6 | Human Klf4 amino acid sequence (NP_004226.3) | MRQPPGESDMAVSDALLPSFSTFASGPAGREKTLRQAGAPNNRWRE<br>ELSHMKRLPPVLPGRPYDLAAATVATDLESGGAGAACGGSNLAPLP<br>RRETEEFNDLLDLDFILSNSLTHPPESVAATVSSSASASSSSSPSS<br>SGPASAPSTCSFTYPIRAGNDPGVAPGGTGGGLLYGRESAPPPTAP<br>FNLADINDVSPSGGFVAELLRPELDPVYIPPQQPQPPGGLMGKFV<br>LKASLSAPGSEYGSPSVISVSKGSPDGSHPVVVAPYNGGPPRTCPK<br>IKQEAVSSCTHLGAGPPLSNGHRPAAHDFPLGRQLPSRTTPTLGLE<br>EVLSSRDCHPALPLPPGFHPHPGPNYPSFLPDQMQPQVPPLHYQEL<br>MPPGSCMPEEPKPKRGRRSWPRKRTATHTCDYAGCGKTYTKSSHLK<br>AHLRTHTGEKPYHCDWDGCGWKFARSDELTRHYRKHTGHRPFQCQK<br>CDRAFSRSDHLALHMKRHF |
| 7 | Human c-Myc gene sequence (NCBI Ref NM_002467) | GACCCCCGAGCTGTGCTGCTCGCGGCCGCCACCGCCGGGCCCCGGC<br>CGTCCCTGGCTCCCCTCCTGCCTCGAGAAGGGCAGGGCTTCTCAGA<br>GGCTTGGCGGGAAAAAGAACGGAGGGAGGGATCGCGCTGAGTATAA<br>AAGCCGGTTTTCGGGGCTTTATCTAACTCGCTGTAGTAATTCCAGC<br>GAGAGGCAGAGGGAGCGAGCGGGCGGCCGGCTAGGGTGGAAGAGCC<br>GGGCGAGCAGAGCTGCGCTGCGGGCGTCCTGGGAAGGGAGATCCGG<br>AGCGAATAGGGGGCTTCGCCTCTGGCCCAGCCCTCCCGCTGATCCC<br>CCAGCCAGCGGTCCGCAACCCTTGCCGCATCCACGAAACTTTGCCC<br>ATAGCAGCGGGCGGGCACTTTGCACTGGAACTTACAACACCCGAGC<br>AAGGACGCGACTCTCCCGACGCGGGGAGGCTATTCTGCCCATTTGG<br>GGACACTTCCCCGCCGCTGCCAGGACCCGCTTCTCTGAAAGGCTCT<br>CCTTGCAGCTGCTTAGACGCTGGATTTTTTTCGGGTAGTGGAAAAC<br>CAGCAGCCTCCCGCGACGATGCCCCTCAACGTTAGCTTCACCAACA<br>GGAACTATGACCTCGACTACGACTCGGTGCAGCCGTATTTCTACTG<br>CGACGAGGAGGAGAACTTCTACCAGCAGCAGCAGCAGAGCGAGCTG<br>CAGCCCCCGGCGCCCAGCGAGGATATCTGGAAGAAATTCGAGCTGC<br>TGCCCACCCCGCCCCTGTCCCCTAGCCGCCGCTCCGGGCTCTGCTC<br>GCCCTCCTACGTTGCGGTCACACCCTTCTCCCTTCGGGGAGACAAC<br>GACGGCGGTGGCGGGAGCTTCTCCACGGCCGACCAGCTGGAGATGG<br>TGACCGAGCTGCTGGGAGGAGACATGGTGAACCAGAGTTTCATCTG<br>CGACCCGGACGACGAGACCTTCATCAAAAACATCATCATCCAGGAC<br>TGTATGTGGAGCGGCTTCTCGGCCGCCGCCAAGCTCGTCTCAGAGA<br>AGCTGGCCTCCTACCAGGCTGCGCGCAAAGACAGCGGCAGCCCGAA<br>CCCCGCCCGCGGCCACAGCGTCTGCTCCACCTCCAGCTTGTACCTG<br>CAGGATCTGAGCGCCGCCGCCTCAGAGTGCATCGACCCCTCGGTGG<br>TCTTCCCCTACCCTCTCAACGACAGCAGCTCGCCCAAGTCCTGCGC<br>CTCGCAAGACTCCAGCGCCTTCTCTCCGTCCTCGGATTCTCTGCTC<br>TCCTCGACGGAGTCCTCCCCGCAGGGCAGCCCCGAGCCCCTGGTGC<br>TCCATGAGGAGACACCGCCCACCACCAGCAGCGACTCTGAGGAGGA<br>ACAAGAAGATGAGGAAGAAATCGATGTTGTTTCTGTGGAAAAGAGG<br>CAGGCTCCTGGCAAAAGGTCAGAGTCTGGATCACCTTCTGCTGGAG<br>GCCACAGCAAACCTCCTCACAGCCCACTGGTCCTCAAGAGGTGCCA<br>CGTCTCCACACATCAGCACAACTACGCAGCGCCTCCCTCCACTCGG<br>AAGGACTATCCTGCTGCCAAGAGGGTCAAGTTGGACAGTGTCAGGA<br>TCCTGAGACAGATCAGCAACAACCGAAAATGCACCAGCCCCAGGTC<br>CTCGGACACCGAGGAGAATGTCAAGAGGCGAACACACAACGTCTTG<br>GAGCGCCAGAGGAGGAACGAGCTAAAACGGAGCTTTTTTGCCCTGC<br>GTGACCAGATCCCGGAGTTGGAAAACAATGAAAAGGCCCCCAAGGT<br>AGTTATCCTTAAAAAAGCCACAGCATACATCCTGTCCGTCCAAGCA<br>GAGGAGCAAAAGCTCATTTCTGAAGAGGACTTGTTGCGGAAACGAC<br>GAGAACAGTTGAAACACAAACTTGAACAGCTACGGAACTCTTGTGC<br>GTAAGGAAAAGTAAGGAAAACGATTCCTTCTAACAGAAATGTCCTG<br>AGCAATCACCTATGAACTTGTTTCAAATGCATGATCAAATGCAACC<br>TCACAACCTTGGCTGAGTCTTGAGACTGAAAGATTTAGCCATAATG<br>TAAACTGCCTCAAATTGGACTTTGGGCATAAAAGAACTTTTTTATG<br>CTTACCATCTTTTTTTTTCTTTAACAGATTTGTATTTAAGAATTG<br>TTTTTAAAAAATTTTAAGATTTACACAATGTTTCTCTGTAAATATT<br>GCCATTAAATGTAAATAACTTTAATAAAACGTTTATAGCAGTTACA<br>CAGAATTTCAATCCTAGTATATAGTACCTAGTATTATAGGTACTAT<br>AAACCCTAATTTTTTTATTTAAGTACATTTTGCTTTTTAAAGTTG<br>ATTTTTTTCTATTGTTTTTAGAAAAAATAAAATAACTGGCAAATAT<br>ATCATTGAGCAAATCTTAAAAAAAAAAAAAAA |
| 8 | Human c-Myc amino acid sequence (NCBI ref NP_002458.2) | MDFFRVVENQQPPATMPLNVSFTNRNYDLDYDSVQPYFYCDEEENF<br>YQQQQQSELQPPAPSEDIWKKFELLPTPPLSPSRRSGLCSPSYVAV<br>TPFSLRGDNDGGGGSFSTADQLEMVTELLGGDMVNQSFICDPDDET<br>FIKNIIIQDCMWSGFSAAAKLVSEKLASYQAARKDSGSPNPARGHS<br>VCSTSSLYLQDLSAAASECIDPSVVFPYPLNDSSSPKSCASQDSSA<br>FSPSSDSLLSSTESSPQGSPEPLVLHEETPPTTSSDSEEEQEDEEE<br>IDVVSVEKRQAPGKRSESGSPSAGGHSKPPHSPLVLKRCHVSTHQH |

TABLE 1-continued

| NO: | Description | Sequence |
|---|---|---|
| | | NYAAPPSTRKDYPAAKRVKLDSVRVLRQISNNRKCTSPRSSDTEEN
VKRRTHNVLERQRRNELKRSFFALRDQIPELENNEKAPKVVILKKA
TAYILSVQAEEQKLISEEDLLRKRREQLKHKLEQLRNSCA |
| 9 | Human Nanog gene sequence (NM_024865.2) | ATTATAAATCTAGAGACTCCAGGATTTTAACGTTCTGCTGGACTGA
GCTGGTTGCCTCATGTTATTATGCAGGCAACTCACTTTATCCCAAT
TTCTTGATACTTTTCCTTCTGGAGGTCCTATTTCTCTAACATCTTC
CAGAAAAGTCTTAAAGCTGCCTTAACCTTTTTTCCAGTCCACCTCT
TAAATTTTTTCCTCCTCTTCCTCTATACTAACATGAGTGTGGATCC
AGCTTGTCCCCAAAGCTTGCCTTGCTTTGAAGCATCCGACTGTAAA
GAATCTTCACCTATGCCTGTGATTTGTGGGCCTGAAGAAAACTATC
CATCCTTGCAAATGTCTTCTGCTGAGATGCCTCACACGGAGACTGT
CTCTCCTCTTCCTTCCTCCATGGATCTGCTTATTCAGGACAGCCCT
GATTCTTCCACCAGTCCCAAAGGCAAACAACCCACTTCTGCAGAGA
AGAGTGTCGCAAAAAAGGAAGACAAGGTCCCGGTCAAGAAACAGAA
GACCAGAACTGTGTTCTCTTCCACCCAGCTGTGTGTACTCAATGAT
AGATTTCAGAGACAGAAATACCTCAGCCTCCAGCAGATGCAAGAAC
TCTCCAACATCCTGAACCTCAGCTACAAACAGGTGAAGACCTGGTT
CCAGAACCAGAGAATGAAATCTAAGAGGTGGCAGAAAAACAACTGG
CCGAAGAATAGCAATGGTGTGACGCAGAAGGCCTCAGCACCTACCT
ACCCCAGCCTTTACTCTTCCTACCACCAGGGATGCCTGGTGAACCC
GACTGGGAACCTTCCAATGTGGAGCAACCAGACCTGGAACAATTCA
ACCTGGAGCAACCAGACCCAGAACATCCAGTCCTGGAGCAACCACT
CCTGGAACACTCAGACCTGGTGCACCCAATCCTGGAACAATCAGGC
CTGGAACAGTCCCTTCTATAACTGTGGAGAGGAATCTGCAGTCC
TGCATGCAGTTCCAGCCAAATTCTCCTGCCAGTGACTTGGAGGCTG
CCTTGGAAGCTGCTGGGGAAGGCCTTAATGTAATACAGCAGACCAC
TAGGTATTTTAGTACTCCACAAACCATGGATTTATTCCTAAACTAC
TCCATGAACATGCAACCTGAAGACGTGTGAAGATGAGTGAAACTGA
TATTACTCAATTTCAGTCTGGACACTGGCTGAATCCTTCCTCTCCC
CTCCTCCCATCCCTCATAGGATTTTTCTTGTTTGGAAACCACGTGT
TCTGGTTTCCATGATGCCCATCCAGTCAATCTCATGGAGGGTGGAG
TATGGTTGGAGCCTAATCAGCGAGGTTTCTTTTTTTTTTTTTTTCC
TATTGGATCTTCCTGGAGAAAATACTTTTTTTTTTTTTTTTTTTGA
AACGGAGTCTTGCTCTGTCGCCCAGGCTGGAGTGCAGTGGCGCGGT
CTTGGCTCACTGCAAGCTCCGTCTCCCGGGTTCACGCCATTCTCCT
GCCTCAGCCTCCCGAGCAGCTGGGACTACAGGCGCCCGCCACCTCG
CCCGGCTAATATTTTGTATTTTTAGTAGAGACGGGGTTTCACTGTG
TTAGCCAGGATGGTCTCGATCTCCTGACCTTGTGATCCACCCGCCT
CGGCCTCCCTAACAGCTGGGATTTACAGGCGTGAGCCACCGCGCCC
TGCCTAGAAAAGACATTTTAATAACCTTGGCTGCCGTCTCTGGCTA
TAGATAAGTAGATCTAATACTAGTTTGGATATCTTTAGGGTTTAGA
ATCTAACCTCAAGAATAAGAAATACAAGTACAAATTGGTGATGAAG
ATGTATTCGTATTGTTTGGGATTGGGAGGCTTTGCTTATTTTTAA
AAACTATTGAGGTAAAGGGTTAAGCTGTAACATACTTAATTGATTT
CTTACCGTTTTTGGCTCTGTTTTGCTATATCCCCTAATTTGTTGGT
TGTGCTAATCTTTGTAGAAAGAGGTCTCGTATTTGCTGCATCGTAA
TGACATGAGTACTGCTTTAGTTGGTTTAAGTTCAAATGAATGAAAC
AACTATTTTTCCTTTAGTTGATTTTACCCTGATTTCACCGAGTGTT
TCAATGAGTAAATATACAGCTTAAACAT |
| 10 | Human Nanog amino acid sequence (NP_079141) | MSVDPACPQSLPCFEASDCKESSPMPVICGPEENYPSLQMSSAEMP
HTETVSPLPSSMDLLIQDSPDSSTSPKGKQPTSAEKSVAKKEDKVP
VKKQKTRTVFSSTQLCVLNDRFQRQKYLSLQQMQELSNILNLSYKQ
VKTWFQNQRMKSKRWQKNNWPKNSNGVTQKASAPTYPSLYSSYHQG
CLVNPTGNLPMWSNQTWNNSTWSNQTQNIQSWSNHSWNTQTWCTQS
WNNQAWNSPFYNCGEESLQSCMQFQPNSPASDLEAALEAAGEGLNV
IQQTTRYFSTPQTMDLFLNYSMNMQPEDV |
| 11 | Human Lin28 gene sequence (NM_024674) | GTGCGGGGGAAGATGTAGCAGCTTCTTCTCCGAACCAACCCTTTGC
CTTCGGACTTCTCCGGGGCCAGCAGCCGCCCGACCAGGGGCCCGGG
GCCACGGGCTCAGCCGACGACCATGGGCTCCGTGTCCAACCAGCAG
TTTGCAGGTGGCTGCGCCAAGGCGGCAGAAGAGGCGCCCGAGGAGG
CGCCGGAGGACGCGGCCCGGGCGGCGGACGAGCCTCAGCTGCTGCA
CGGTGCGGGCATCTGTAAGTGGTTCAACGTGCGCATGGGGTTCGGC
TTCCTGTCCATGACCGCCCGCGCCGGGGTCGCGCTCGACCCCCCAG
TGGATGTCTTTGTGCACCAGAGTAAGCTGCACATGGAAGGGTTCCG
GAGCTTGAAGGAGGGTGAGGCAGTGGAGTTCACCTTTAAGAAGTCA
GCCAAGGGTCTGGAATCCATCCGTGTCACCGGACCTGGTGGAGTAT
TCTGTATTGGGAGTGAGAGGCGGCCAAAAGGAAAGAGCATGCAGAA
GCGCAGATCAAAAGGAGACAGGTGCTACAACTGTGGAGGTCTAGAT
CATCATGCCAAGGAATGCAAGCTGCCACCCCAGCCCAAGAAGTGCC
ACTTCTGCCAGAGCATCAGCCATATGGTAGCCTCATGTCCGCTGAA
GGCCCAGCAGGGCCCTAGTGCACAGGGAAAGCCAACCTACTTTCGA
GAGGAAGAAGAAGAAATCCACAGCCCTACCCTGCTCCCGGAGGCAC
AGAATTGAGCCACAATGGGTGGGGGCTATTCTTTTGCTATCAGGAA
GTTTTGAGGAGCAGGCAGAGTGGAGAAAGTGGGAATAGGGTGCATT
GGGGCTAGTTGGCACTGCCATGTATCTCAGGCTTGGGTTCACACCA |

TABLE 1-continued

| NO: | Description | Sequence |
|---|---|---|
| | | TCACCCTTTCTTCCCTCTAGGTGGGGGGAAAGGGTGAGTCAAAGGA |
| | | ACTCCAACCATGCTCTGTCCAAATGCAAGTGAGGGTTCTGGGGGCA |
| | | ACCAGGAGGGGGAATCACCCTACAACCTGCATACTTTGAGTCTCC |
| | | ATCCCCAGAATTTCCAGCTTTTGAAAGTGGCCTGGATAGGGAAGTT |
| | | GTTTTCCTTTTAAAGAAGGATATATAATAATTCCCATGCCAGAGTG |
| | | AAATGATTAAGTATAAGACCAGATTCATGGAGCCAAGCCACTACAT |
| | | TCTGTGGAAGGAGATCTCTCAGGAGTAAGCATTGTTTTTTTTTCAC |
| | | ATCTTGTATCCTCATACCCACTTTTGGGATAGGGTGCTGGCAGCTG |
| | | TCCCAAGCAATGGGTAATGATGATGGCAAAAGGGTGTTTGGGGGA |
| | | ACAGCTGCAGACCTGCTGCTCTATGCTCACCCCCGCCCCATTCTGG |
| | | GCCAATGTGATTTTATTTATTTGCTCCCTTGGATACTGCACCTTGG |
| | | GTCCCACTTTCTCCAGGATGCCAACTGCACTAGCTGTGTGCGAATG |
| | | ACGTATCTTGTGCATTTTAACTTTTTTTCCTTAATATAAATATTCT |
| | | GGTTTTGTATTTTGTATATTTTAATCTAAGGCCCTCATTTCCTGC |
| | | ACTGTGTTCTCAGGTACATGAGCAATCTCAGGGATAGCCAGCAGCA |
| | | GCTCCAGGTCTGCGCAGCAGGAATTACTTTTTGTTGTTTTTGCCAC |
| | | CGTGGAGAGCAACTATTTGGAGTGCACAGCCTATTGAACTACCTCA |
| | | TTTTTGCCAATAAGAGCTGGCTTTTCTGCCATAGTGTCCTCTTGAA |
| | | ACCCCCTCTGCCTTGAAAATGTTTTATGGGAGACTAGGTTTTAACT |
| | | GGGTGGCCCCATGACTTGATTGCCTTCTACTGGAAGATTGGGAATT |
| | | AGTCTAAACAGGAAATGGTGGTACACAGAGGCTAGGAGAGGCTGGG |
| | | CCCGGTGAAAAGGCCAGAGAGCAAGCCAAGATTAGGTGAGGGTTGT |
| | | CTAATCCTATGGCACAGGACGTGCTTTACATCTCCAGATCTGTTCT |
| | | TCACCAGATTAGGTTAGGCCTACCATGTGCCACAGGGTGTGTGTGT |
| | | GTTTGTAAAACTAGAGTTGCTAAGGATAAGTTTAAAGACCAATACC |
| | | CCTGTACTTAATCCTGTGCTGTCGAGGGATGGATATATGAAGTAAG |
| | | GTGAGATCCTTAACCTTTCAAAATTTTCGGGTTCCAGGGAGACACA |
| | | CAAGCGAGGGTTTTGTGGTGCCTGGAGCCTGTGTCCTGCCCTGCTA |
| | | CAGTAGTGATTAATAGTGTCATGGTAGCTAAAGGAGAAAAAGGGGG |
| | | TTTCGTTTACACGCTGTGAGATCACCGCAAACCTACCTTACTGTGT |
| | | TGAAACGGGACAAATGCAATAGAACGCATTGGGTGGTGTGTGTCTG |
| | | ATCCTGGGTTCTTGTCTCCCCTAAATGCTGCCCCCCAAGTTACTGT |
| | | ATTTGTCTGGGCTTTGTAGGACTTCACTACGTTGATTGCTAGGTGG |
| | | CCTAGTTTGTGTAAATATAATGTATTGGTCTTTCTCCGTGTTCTTT |
| | | GGGGGTTTTGTTTACAAACTTCTTTTTGTATTGAGAGAAAAATAGC |
| | | CAAAGCATCTTTGACAGAAGGTTCTGCACCAGGCAAAAAGATCTGA |
| | | AACATTAGTTTGGGGGGCCCTCTTCTTAAAGTGGGGATCTTGAACC |
| | | ATCCTTTCTTTTGTATTCCCCTTCCCCTATTACCTATTAGACCAGA |
| | | TCTTCTGTCCTAAAAACTTGTCTTCTACCCTGCCCTCTTTTCTGTT |
| | | CACCCCCAAAAGAAAACTTACACACCCACACACATACACATTTCAT |
| | | GCTTGGAGTGTCTCCACAACTCTTAAATGATGTATGCAAAAATACT |
| | | GAAGCTAGGAAAACCCTCCATCCCTTGTTCCCAACCTCCTAAGTCA |
| | | AGACCATTACCATTTCTTTCTTTCTTTTTTTTTTTTTTAAAATG |
| | | GAGTCTCACTGTGTCACCCAGGCTGGAGTGCAGTGGCATGATCGGC |
| | | TCACTGCAGCCTCTGCCTCTTGGGTTCAAGTGATTCTCCTGCCTCA |
| | | GCCTCCTGAGTAGCTGGGATTTCAGGCACCCGCCACACTCAGCTAA |
| | | TTTTTGTATTTTTAGTAGAGACGGGGTTTCACCATGTTGTCCAGGC |
| | | TGGTCTGGAACTCCTGACCTCAGGTGATCTGCCCACCTTGGCTTCC |
| | | CAAAGTGCTGGGATTACAGGCATGAGCCACCATGCTGGGCCAACCA |
| | | TTTCTTGGTGTATTCATGCCAAACACTTAAGACACTGCTGTAGCCC |
| | | AGGCGCGGTGGCTCACACCTGTAATCCCAGCACTTTGGAAGGCTGA |
| | | GGCGGGCGGATCACAAGGTCACGAGTTCAAAACTATCCTGGCCAAC |
| | | ACAGTGAAACCCCGTCTCTACTAAAATACAAAAAAATTAGCCGGGT |
| | | GTGGTGGTGCATGCCTTTAGTCCTAGCTATTCAGGAGGCTGAGGCA |
| | | GGGGAATCGCTTGAACCCGAGAGGCAGAGGTTGCAGTGAGCTGAGA |
| | | TCGCACCACTGCACTCCAGCCTGGTTACAGAGCAAGACTCTGTCTC |
| | | AAACAAAACAAAACAAAACAAAAACACACTACTGTATTTTGGATGG |
| | | ATCAAACCTCCTTAATTTTAATTTCTAATCCTAAAGTAAAGAGATG |
| | | CAATTGGGGGCCTTCCATGTAGAAAGTGGGGTCAGGAGGCCAAGAA |
| | | AGGGAATATGAATGTATATCCAAGTCACTCAGGAACTTTTATGCAG |
| | | GTGCTAGAAACTTTATGTCAAAGTGGCCACAAGATTGTTTAATAGG |
| | | AGACGAACGAATGTAACTCCATGTTTACTGCTAAAAACCAAAGCTT |
| | | TGTGTAAAATCTTGAATTTATGGGCGGGAGGGTAGGAAAGCCTGT |
| | | ACCTGTCTGTTTTTTCCTGATCCTTTTCCCTCATTCCTGAACTGC |
| | | AGGAGACTGAGCCCCTTTGGGCTTTGGTGACCCCATCACTGGGGTG |
| | | TGTTTATTTGATGGTTGATTTTGCTGTACTGGGTACTTCCTTTCCC |
| | | ATTTTCTAATCATTTTTTAACACAAGCTGACTCTTCCCTTCCCTTC |
| | | TCCTTTCCCTGGGAAATACAATGAATAAATAAAGACTTATTGGTA |
| | | CGCAAACTGTCA |
| 12 | Human Lin28 amino acid sequence (NP_078950) | MGSVSNQQFAGGCAKAAEEAPEEAPEDAARAADEPQLLHGAGICKW FNVRMGFGFLSMTARAGVALDPPVDVFVHQSKLHMEGFRSLKEGEA VEFTFKKSAKGLESIRVTGPGGVFCIGSERRPKGKSMQKRRSKGDR CYNCGGLDHHAKECKLPPQPKKCHFCQSISHMVASCPLKAQQGPSA QGKPTYFREEEEEIHSPTLLPEAQN |

REFERENCES

1. Takahashi, K. & Yamanaka, S., Induction of pluripotent stem cells from mouse embryonic and adult fibroblast cultures by defined factors. *Cell* 126 (4), 663-676 (2006).
2. Takahashi, K. et al., Induction of pluripotent stem cells from adult human fibroblasts by defined factors. *Cell* 131 (5), 861-872 (2007).
3. Yu, J. et al., Induced pluripotent stem cell lines derived from human somatic cells. *Science* 318 (5858), 1917-1920 (2007).
4. Marion, R. M. et al., A p53-mediated DNA damage response limits reprogramming to ensure iPS cell genomic integrity. *Nature* 460 (7259), 1149-1153 (2009).
5. Li, H. et al., The Ink4/Arf locus is a barrier for iPS cell reprogramming. *Nature* 460 (7259), 1136-1139 (2009).
6. Banito, A. et al., Senescence impairs successful reprogramming to pluripotent stem cells. *Genes Dev* 23 (18), 2134-2139 (2009).
7. Utikal, J. et al., Immortalization eliminates a roadblock during cellular reprogramming into iPS cells. *Nature* 460 (7259), 1145-1148 (2009).
8. Kawamura, T. et al., Linking the p53 tumour suppressor pathway to somatic cell reprogramming. *Nature* 460 (7259), 1140-1144 (2009).
9. Campisi, J. & d'Adda di Fagagna, F., Cellular senescence: when bad things happen to good cells. *Nat Rev Mol Cell Biol* 8 (9), 729-740 (2007).
10. Collado, M., Blasco, M. A., & Serrano, M., Cellular senescence in cancer and aging. *Cell* 130 (2), 223-233 (2007).
11. Zhang, R., Chen, W., & Adams, P. D., Molecular dissection of formation of senescence-associated heterochromatin foci. *Mol Cell Biol* 27 (6), 2343-2358 (2007).
12. Liao, J. et al., Enhanced efficiency of generating induced pluripotent stem (iPS) cells from human somatic cells by a combination of six transcription factors. *Cell Res* 18 (5), 600-603 (2008).
13. Hanna, J. et al., Direct cell reprogramming is a stochastic process amenable to acceleration. *Nature* 462 (7273), 595-601 (2009).
14. Yu, J. et al., Human Induced Pluripotent Stem Cells Free of Vector and Transgene Sequences. *Science* (2009).
15. Krishnamurthy, J. et al., Ink4a/Arf expression is a biomarker of aging. *J Clin Invest* 114 (9), 1299-1307 (2004).
16. Zhang, W. et al., Comparison of global DNA methylation profiles in replicative versus premature senescence. *Life Sci* 83 (13-14), 475-480 (2008).
17. Marion, R. M. et al., Telomeres acquire embryonic stem cell characteristics in induced pluripotent stem cells. *Cell Stem Cell* 4 (2), 141-154 (2009).
18. Assou, S. et al., A meta-analysis of human embryonic stem cells transcriptome integrated into a web-based expression atlas. *Stem Cells* 25 (4), 961-973 (2007).
19. Guenther, M. G. et al., Chromatin structure and gene expression programs of human embryonic and induced pluripotent stem cells. *Cell Stem Cell* 7 (2), 249-257.
20. Passos, J. F. et al., Mitochondrial dysfunction accounts for the stochastic heterogeneity in telomere-dependent senescence. *PLoS Biol* 5 (5), e110 (2007).
21. Moiseeva, O., Bourdeau, V., Roux, A., Deschenes-Simard, X., & Ferbeyre, G., Mitochondrial dysfunction contributes to oncogene-induced senescence. *Mol Cell Biol* 29 (16), 4495-4507 (2009).
22. Prigione, A., Fauler, B., Lurz, R., Lehrach, H., & Adjaye, J., The senescence-related mitochondrial/oxidative stress pathway is repressed in human induced pluripotent stem cells. *Stem Cells* 28 (4), 721-733 (2010).
23. Park, I. H. et al., Reprogramming of human somatic cells to pluripotency with defined factors. *Nature* 451 (7175), 141-146 (2008).
24. Assou, S. et al., A gene expression signature shared by human mature oocytes and embryonic stem cells. *BMC Genomics* 10, 10 (2009).
25. Matsuura, F. et al., Senescent phenotypes of skin fibroblasts from patients with Tangier disease. *Biochemical and biophysical research communications* 357 (2), 493-498 (2007).
26. Ludwig, T. E. et al., Feeder-independent culture of human embryonic stem cells. *Nat Methods* 3 (8), 637-646 (2006).
27. Freberg, C. T., Dahl, J. A., Timoskainen, S., & Collas, P., Epigenetic Reprogramming of OCT4 and NANOG regulatory regions by embryonal carcinoma cell extract. *Molecular biology of the cell* 18 (5), 1543-1553 (2007).

The invention claimed is:

1. An ex vivo method for preparing rejuvenated induced pluripotent stem cells (iPSCs) from senescent cells, said method comprising the steps of:
   a) providing said senescent cells and,
   b) culturing said target cell population under appropriate conditions for reprogramming said target cell population into iPSCs, wherein said appropriate conditions comprise increasing expression in said target cell population, of at least the following combination of reprogramming factors:
      i. a reprogramming factor encoded by one gene of the Oct gene family,
      ii. a reprogramming factor encoded by one gene of the Klf gene family,
      iii. a reprogramming factor encoded by one gene of the Sox gene family, iv. a reprogramming factor encoded by one gene of the Myc gene family,
      v. Lin28,
      vi. and Nanog,
      wherein the method results in preparation of rejuvenated iPSC cells in which the expression of p21$^{CIP1}$ and p16$^{IN1K4A}$ is downregulated to a level found in human embryonic stem cells (hESC).

2. The method of claim 1, wherein said combination of reprogramming factors comprises Oct4, Klf4, Sox2, c-Myc, Lin28 and Nanog.

3. The method of claim 1, wherein said senescent cells are:
   a. human senescent cells;
   b. human senescent cells obtained from an adult subject that is at least 50 years old; or
   c. human senescent cells obtained from a subject suffering from age-related disorders leading to a high proportion of senescent cells.

4. The method of claim 1, wherein said method does not further comprise a step of silencing senescence effectors in said senescent cells.

5. The method of claim 4, wherein said senescence effectors include p21$^{CIP}$ and/or p16$^{INK4a}$ and/or p53.

6. The method according to claim 1, wherein said conditions for increasing expression of the reprogramming factors comprise
   a) introducing one or more expression vectors comprising coding sequences of said combination of reprogramming factors into said senescent cells; or,
   b) directly delivering an effective amount of each precursor RNA of the reprogramming factors into said senescent cells.

7. The method of claim 6, wherein said step of introducing is performed by transfecting said senescent cells with said one or more expression vectors.

8. An in vitro method for rejuvenating senescent cells, said method comprising the step of reprogramming said cells to induced pluripotent stem cells iPSCs, by increasing expression in said cells of at least a combination of the following reprogramming factors:
i. a reprogramming factor encoded by one gene of the Oct gene family,
ii. a reprogramming factor encoded by one gene of the Klf gene family,
iii. a reprogramming factor encoded by one gene of the Sox gene family,
iv. a reprogramming factor encoded by one gene of the Myc gene family, Lin28,
v. and Nanog.

9. The method of claim 8, wherein said step of reprogramming includes a step of culturing said cells under appropriate conditions for increasing expression of the following reprogramming factors: Oct4, Klf4, Sox2, c-Myc, Lin28 and Nanog.

10. The method of claim 3, wherein said human senescent cells are human fibroblast senescent cells.

11. The method according to claim 1, wherein said senescent cells provided at step (a) are comprised in a cell composition obtained from an adult subject that is at least 50 years old.

12. The method of claim 8, wherein said senescent cells are comprised in a cell composition obtained from an adult subject that is at least 50 years old.

* * * * *